United States Patent
Alva

(10) Patent No.: US 9,155,339 B2
(45) Date of Patent: Oct. 13, 2015

(54) GARMENTS FOR A NURSING WOMAN

(71) Applicant: Dawn Michele Alva, Marina, CA (US)

(72) Inventor: Dawn Michele Alva, Marina, CA (US)

(*) Notice: Subject to any disclaimer, the term of this patent is extended or adjusted under 35 U.S.C. 154(b) by 0 days.

(21) Appl. No.: 14/172,537

(22) Filed: Feb. 4, 2014

(65) Prior Publication Data

US 2014/0220860 A1    Aug. 7, 2014

Related U.S. Application Data

(60) Provisional application No. 61/849,874, filed on Feb. 4, 2013.

(51) Int. Cl.
*A41C 3/00* (2006.01)
*A41C 3/04* (2006.01)
*A41D 1/20* (2006.01)

(52) U.S. Cl.
CPC .. *A41C 3/04* (2013.01); *A41D 1/205* (2013.01)

(58) Field of Classification Search
CPC ......... A41C 3/005; A41C 3/0057; A41C 3/04
USPC .................. 450/7–11, 15–18, 23–28, 30–35, 450/64–66; 2/106, 105, 73, 74.1–74.4, 104
See application file for complete search history.

(56) References Cited

U.S. PATENT DOCUMENTS

| 155,720 | A |   | 10/1874 | Gray et al. |       |
|---------|---|---|---------|-------------|-------|
| 238,945 | A | * | 3/1881  | Marks       | 2/93  |
| 277,744 | A | * | 5/1883  | Kimball     | 2/128 |
| 614,068 | A | * | 11/1898 | Wetzler     | 2/102 |
| 684,078 | A |   | 10/1901 | Martin      |       |
| 689,699 | A | * | 12/1901 | Bandler     | 86/36 |
| 949,414 | A |   | 2/1910  | Cunningham  |       |
| 1,136,727 | A |  | 4/1915 | Smith       |       |
| 1,189,589 | A |  | 7/1916 | Lawrence    |       |
| 1,371,841 | A | * | 3/1921 | Berkwits   | 2/93  |
| 1,509,226 | A |  | 9/1924 | Brown       |       |
| 1,670,610 | A |  | 5/1928 | Colby       |       |
| 1,849,514 | A | * | 3/1932 | Edelmann   | 450/91 |

(Continued)

FOREIGN PATENT DOCUMENTS

| AU | 2006200947 A1 | 9/2006 |
| DE | 584456 C | 9/1933 |
| EP | 0 752 213 A1 | 1/1997 |
| EP | 0 941 674 A1 | 9/1999 |

(Continued)

OTHER PUBLICATIONS

International Search Report for PCT/US2010/053075, (dated Jan. 24, 2011), 5 pages.
Written Opinion for PCT/US2010/053075, (dated Jan. 24, 2011), 6 pages.
Decker, C., "Hands-free Breast Pumping Tip," babylovesyourmilk. com, (last modified Jun. 4, 2010), http://babylovesyourmilk.com/hands-free-breast-pumping.php, 4 pages.

*Primary Examiner* — Gloria Hale
(74) *Attorney, Agent, or Firm* — TraskBritt

(57) ABSTRACT

A garment for a nursing woman includes at least partially overlapping layers of material. The layers extend between lateral sides of the garment. Some edges of the layers may be attached to edges of other layers or components, while at least one edge of each layer is a free edge. Free edges at least partially define nooks into which the funnels of breast pumps may be received. The free edges of the garment provide multi-directional support to the funnels to enable hands-free pumping. In some embodiments, medial edges of components of the garment cross one another and extend to contribute to the support of the funnels during use of the garment.

20 Claims, 31 Drawing Sheets

(56) References Cited

U.S. PATENT DOCUMENTS

| | | | |
|---|---|---|---|
| 2,075,656 A * | 3/1937 | Paternayan | 112/197 |
| 2,236,142 A * | 3/1941 | Kaupp | 450/5 |
| 2,298,361 A | 10/1942 | Freund | |
| 2,436,430 A | 2/1948 | Hart | |
| 2,440,466 A | 4/1948 | Freedman | |
| 2,452,345 A | 10/1948 | Anselmo | |
| 2,485,313 A | 10/1949 | Rabinowitz | |
| 2,486,836 A * | 11/1949 | Garson | 450/91 |
| 2,492,862 A | 12/1949 | Harvey | |
| 2,498,487 A | 2/1950 | Elias | |
| 2,501,860 A | 3/1950 | Becker | |
| 2,585,338 A | 2/1952 | Meares | |
| 2,611,130 A * | 9/1952 | Engelman | 450/30 |
| 2,613,355 A | 10/1952 | Coleman | |
| D170,509 S | 9/1953 | Peck | |
| 2,679,048 A | 5/1954 | Alberts | |
| 2,711,539 A * | 6/1955 | Loscher | 2/93 |
| 2,715,225 A | 8/1955 | Gould | |
| 2,890,702 A | 6/1959 | Farino | |
| 2,925,816 A | 2/1960 | Rosenthal | |
| 2,928,396 A | 3/1960 | O'Dell | |
| 3,002,515 A | 10/1961 | Glogover | |
| 3,145,714 A | 8/1964 | Brown | |
| 3,306,299 A | 2/1967 | Paramore | |
| 3,516,415 A | 6/1970 | Hadley-Webb | |
| 3,524,449 A * | 8/1970 | Peters | 450/100 |
| 3,746,007 A | 7/1973 | Hand et al. | |
| 3,746,008 A | 7/1973 | LoCascio et al. | |
| 3,763,865 A | 10/1973 | DeFru | |
| 3,773,052 A | 11/1973 | Belardinelli | |
| 3,780,741 A | 12/1973 | Cole | |
| 3,782,385 A | 1/1974 | Loyd | |
| 3,834,397 A | 9/1974 | Birch | |
| 3,840,012 A | 10/1974 | Rushton, Jr. | |
| 3,890,978 A | 6/1975 | Nobbs | |
| 3,931,816 A * | 1/1976 | Waldmann | 602/19 |
| 4,004,294 A | 1/1977 | Pinch | |
| 4,263,912 A | 4/1981 | Adams | |
| 4,270,538 A | 6/1981 | Murphy | |
| 4,335,728 A | 6/1982 | Fildan | |
| 4,355,641 A | 10/1982 | Dastoli et al. | |
| 4,390,024 A | 6/1983 | Williams et al. | |
| 4,393,875 A | 7/1983 | O'Boyle et al. | |
| 4,411,269 A | 10/1983 | Weintraub | |
| 4,423,734 A | 1/1984 | Schawel | |
| 4,453,549 A | 6/1984 | DiTullio | |
| 4,550,734 A | 11/1985 | Porco | |
| 4,584,992 A | 4/1986 | Liu | |
| 4,633,876 A | 1/1987 | Scullin | |
| 4,640,287 A | 2/1987 | Anderson et al. | |
| 4,673,388 A | 6/1987 | Schlensog et al. | |
| 4,697,592 A * | 10/1987 | Maddux et al. | 450/155 |
| 4,713,842 A | 12/1987 | Patterson | |
| 4,857,051 A | 8/1989 | Larsson | |
| 4,878,879 A | 11/1989 | Kunstadter | |
| 4,892,517 A | 1/1990 | Yuan et al. | |
| 4,911,677 A | 3/1990 | White | |
| 4,929,229 A | 5/1990 | Larsson | |
| 5,009,638 A | 4/1991 | Riedweg et al. | |
| 5,024,628 A | 6/1991 | Sanchez | |
| 5,032,104 A | 7/1991 | Rainville | |
| 5,038,411 A | 8/1991 | St. Armand | |
| 5,045,019 A | 9/1991 | Capasso et al. | |
| 5,049,126 A | 9/1991 | Larsson | |
| D321,273 S | 11/1991 | Hull | |
| 5,071,403 A | 12/1991 | Larsson | |
| 5,090,059 A | 2/1992 | Kahl | |
| 5,092,812 A | 3/1992 | Babcock | |
| 5,094,647 A | 3/1992 | Courtney | |
| 5,167,566 A | 12/1992 | Novitsky et al. | |
| 5,180,326 A * | 1/1993 | Williams | 450/91 |
| 5,278,998 A | 1/1994 | Book | |
| 5,295,957 A | 3/1994 | Aida et al. | |
| 5,309,572 A | 5/1994 | Seamans | |
| 5,358,476 A | 10/1994 | Wilson | |
| 5,380,238 A | 1/1995 | Crew-Gee | |
| 5,415,632 A | 5/1995 | Samson | |
| D366,351 S | 1/1996 | Winchell | |
| 5,514,166 A | 5/1996 | Silver et al. | |
| 5,571,084 A | 11/1996 | Palmer | |
| 5,575,768 A | 11/1996 | Lockridge et al. | |
| 5,616,125 A | 4/1997 | Jelks | |
| 5,660,577 A | 8/1997 | Modena | |
| 5,664,257 A | 9/1997 | Hall | |
| 5,697,830 A | 12/1997 | White | |
| 5,720,722 A | 2/1998 | Lockridge | |
| 5,823,851 A * | 10/1998 | Dicker | 450/2 |
| 5,941,847 A | 8/1999 | Huber et al. | |
| 5,954,690 A | 9/1999 | Larsson | |
| 6,004,186 A | 12/1999 | Penny | |
| 6,027,396 A | 2/2000 | Yonchar | |
| 6,083,079 A | 7/2000 | Pearson | |
| 6,178,784 B1 * | 1/2001 | Marley, Jr. | 66/173 |
| 6,213,840 B1 | 4/2001 | Han | |
| 6,227,936 B1 | 5/2001 | Mendoza | |
| 6,247,996 B1 | 6/2001 | Fields | |
| D446,629 S | 8/2001 | Swanger | |
| 6,346,027 B1 | 2/2002 | Merkovsky | |
| 6,379,327 B2 | 4/2002 | Lundy | |
| 6,440,100 B1 | 8/2002 | Prentiss | |
| 6,575,202 B2 | 6/2003 | Lafond | |
| 6,652,484 B1 | 11/2003 | Hunckler et al. | |
| 6,659,841 B2 | 12/2003 | Raimondo | |
| 6,706,012 B2 | 3/2004 | McKendry et al. | |
| 6,764,377 B2 | 7/2004 | Gillan | |
| 6,821,185 B1 | 11/2004 | Francis | |
| 6,854,132 B1 * | 2/2005 | Polzin | 2/104 |
| 6,855,029 B2 | 2/2005 | Rothman | |
| 6,866,558 B2 | 3/2005 | Luciano et al. | |
| 6,887,217 B1 | 5/2005 | Logan | |
| 6,896,581 B2 | 5/2005 | Otto | |
| 6,974,361 B2 | 12/2005 | Cravaack et al. | |
| 7,076,809 B2 | 7/2006 | Rothman | |
| 7,094,217 B2 | 8/2006 | Fialkoff | |
| 7,128,877 B2 | 10/2006 | Quay et al. | |
| 7,223,255 B2 | 5/2007 | Myers et al. | |
| 7,435,155 B2 | 10/2008 | Reinisch et al. | |
| 7,448,936 B1 | 11/2008 | Kemp-Dorsey | |
| 7,559,915 B2 | 7/2009 | Dao et al. | |
| 7,695,343 B2 | 4/2010 | Nobbs | |
| 8,137,153 B2 | 3/2012 | Bell | |
| 8,192,247 B2 | 6/2012 | Abbaszadeh | |
| 8,307,463 B2 | 11/2012 | Ritchie | |
| 8,323,070 B2 | 12/2012 | Abbaszadeh | |
| 8,414,353 B1 | 4/2013 | Leavell | |
| 8,469,770 B2 | 6/2013 | Alva | |
| 2002/0022433 A1 * | 2/2002 | Yeung et al. | 450/70 |
| 2002/0193811 A1 | 12/2002 | Myers et al. | |
| 2003/0167037 A1 | 9/2003 | Fialkoff | |
| 2003/0191427 A1 | 10/2003 | Jay et al. | |
| 2005/0159701 A1 | 7/2005 | Conaway | |
| 2006/0111664 A1 | 5/2006 | Samson et al. | |
| 2007/0161330 A1 | 7/2007 | Whitehead et al. | |
| 2008/0039781 A1 | 2/2008 | Bjorge | |
| 2010/0159802 A1 | 6/2010 | Abbaszadeh | |
| 2011/0239702 A1 | 10/2011 | Best et al. | |
| 2011/0314587 A1 | 12/2011 | Ritchie | |
| 2012/0184179 A1 | 7/2012 | Blitz | |
| 2012/0197187 A1 | 8/2012 | LaFave | |
| 2012/0277636 A1 | 11/2012 | Blondheim et al. | |
| 2012/0309264 A1 | 12/2012 | Kubik | |
| 2013/0095727 A1 | 4/2013 | Abbaszadeh | |

FOREIGN PATENT DOCUMENTS

| | | |
|---|---|---|
| FR | 1.004.058 A | 3/1952 |
| GB | 2 287 640 A | 9/1995 |
| WO | 9953780 A1 | 10/1999 |
| WO | 2009134274 A1 | 11/2009 |
| WO | 2010070042 A1 | 6/2010 |
| WO | 2010080122 A1 | 7/2010 |
| WO | 2012172437 A2 | 12/2012 |

* cited by examiner

GARMENTS FOR A NURSING WOMAN

CROSS-REFERENCE TO RELATED APPLICATION

This application claims the benefit of U.S. Provisional Patent Application Ser. No. 61/849,874, filed Feb. 4, 2013, the disclosure of which is incorporated herein in its entirety by this reference.

TECHNICAL FIELD

The present disclosure, in various embodiments, relates generally to apparel worn by a nursing woman. More particularly, this disclosure relates to a garment configured to accommodate a woman's use of a breast pump, nursing of an infant by the woman, or both.

BACKGROUND

Because of the increased awareness of the health benefits of breastfeeding for both infant and mother, many women are finding ways to provide their infants with breast milk even if the mothers are not physically present during the delivery of the milk to the infants or not physically able to directly breastfeed their infants. To do this, typically, a woman will express milk using a manual or electric breast pump device that has a funnel. The funnel is placed over the nipple of the breast, and suction is applied by the breast pump to encourage expression of milk from the nipple. A traditional electronic breast pump includes the funnel, a motor to generate the suction for the expression of milk, and a reservoir connected to the funnel to receive the expressed milk. Because of the duration and frequency required for breast milk expression, a woman may express both breasts simultaneously to increase efficiency. This process is often uncomfortable and time consuming. Further, without additional support, the funnel of a traditional breast pump often will not remain over the nipple on the breast; therefore, use of the pump often inhibits the woman from concurrently performing other activities.

Efforts have been made to design brassieres that may be adjusted to give an infant access to a nursing woman's breast. For example, U.S. Pat. No. 2,501,860, issued Mar. 28, 1950, describes a brassiere with cups that allow an infant access to the woman's breasts. Access is provided by the woman detaching a flap of the brassiere at the top of each cup and folding back the fabric to reveal an opening in the fabric. The opening exposes the full breast and allows the infant to breastfeed from the mother.

Other conventional nursing garments may be configured for use with a breast pump. These designs are often uncomfortable and cumbersome for the nursing woman. Often, the conventional garments include various attachments to secure a funnel of a breast pump to the wearer's breast. For example, elastic bands, slings, hooks, buttons, and the like may be used. Some conventional garments require additional devices or fabric pieces to be added or detached before the funnel can be secured. For example, U.S. Pat. No. 7,094,217, issued Aug. 22, 2006, describes the use of an elastic band to secure a funnel of a pump and the use of a latch to secure portions of the brassiere when the wearer is not expressing milk.

Many conventional nursing brassieres are not designed to be worn for an extended length of time, but rather, essentially only while the wearer is expressing milk. Often, donning such brassieres or attaching breast pumps, for the time of nursing, requires at least partially disrobing or at least partial exposure of the breast. For example, U.S. Pat. No. 6,004,186, issued Dec. 21, 1999, describes a garment (e.g., a halter top, a bandeau, a tube top) that the woman wears to secure a funnel of a breast pump to her breast. Breast pump funnels may be inserted into two openings in a central area of each side of the garment.

Conventional nursing brassieres also may not be configured to accommodate attachment and detachment of breast pump funnels while the woman is wearing the brassiere, may not accommodate or support the natural expansion and contraction of a nursing woman's breasts, and may not be designed to accommodate both direct nursing of an infant and pumping of breast milk with a breast pump.

BRIEF SUMMARY

Garments of the present disclosure enable engagement of one or more funnels of one or more breast pumps. Embodiments of the present disclosure may enable such engagement without slings, hooks, buttons, hook-and-loop attachments, latches, or the like to secure a funnel to a breast. In some embodiments, separate devices or material pieces may not need to be added or detached to enable access to the breast by either the funnel or an infant. Garments of the present disclosure may enable engagement with and disengagement of the funnel without disrobing and while the woman is wearing the garment, which may reduce the risk of spilling expressed milk; the garments of the present disclosure may also be worn as a functional undergarment for an extended length of time. Embodiments of the present disclosure may not define permanent holes or openings at the center of each side (e.g., at the center of each cup) of the garment and may support the breasts while accommodating the natural expansion and contraction of a nursing woman's breasts. The garments may also enable direct breastfeeding of an infant, in addition to enabling hands-free pumping (i.e., pumping of milk without supporting, with one's hand or hands, the reservoir of the pump throughout the pumping). Embodiments of the present disclosure may include outer and inner material layers that are seamless and continuous and that fully cover the breast and nipple without openings in the layers at the nipple. Moreover, embodiments of the present disclosure may include free edges that may be manipulated to define an opening for the funnel and enable positioning of the funnel anywhere on the breast.

Accordingly, disclosed is a garment for a nursing woman. The garment comprises material layers extending between a lateral side of the garment, another lateral side of the garment, and one of a pair of shoulder straps of the garment. The material layers at least partially overlap one another to define a nook proximate the lateral side of the garment and to define another nook proximate the another lateral side of the garment.

Also disclosed is a garment for a nursing woman that comprises outer material layers and inner material layers. The outer material layers extend between lateral sides of the garment. The inner material layers each extend from one of the lateral sides of the garment to a free peripheral edge that is medially disposed to another of the lateral sides of the garment.

Moreover, disclosed is a garment for a nursing woman. The garment comprises a left-chest component and a right-chest component. The left-chest component comprises a left outer material layer and a left inner material layer. The left outer material layer and the left inner material layer are attached to one another along at least one attached peripheral edge of the left-chest component. The left outer material layer at least partially overlays a free peripheral edge of the left inner material layer. The right-chest component comprises a right outer material layer and a right inner material layer. The right outer material layer and the right inner material layer are attached to one another along at least one attached peripheral edge of the right-chest component. The right outer material layer at least partially overlays a free peripheral edge of the right inner material layer. A medial edge of the left-chest component crosses a medial edge of the right-chest component.

DETAILED DESCRIPTION

Figure 1:
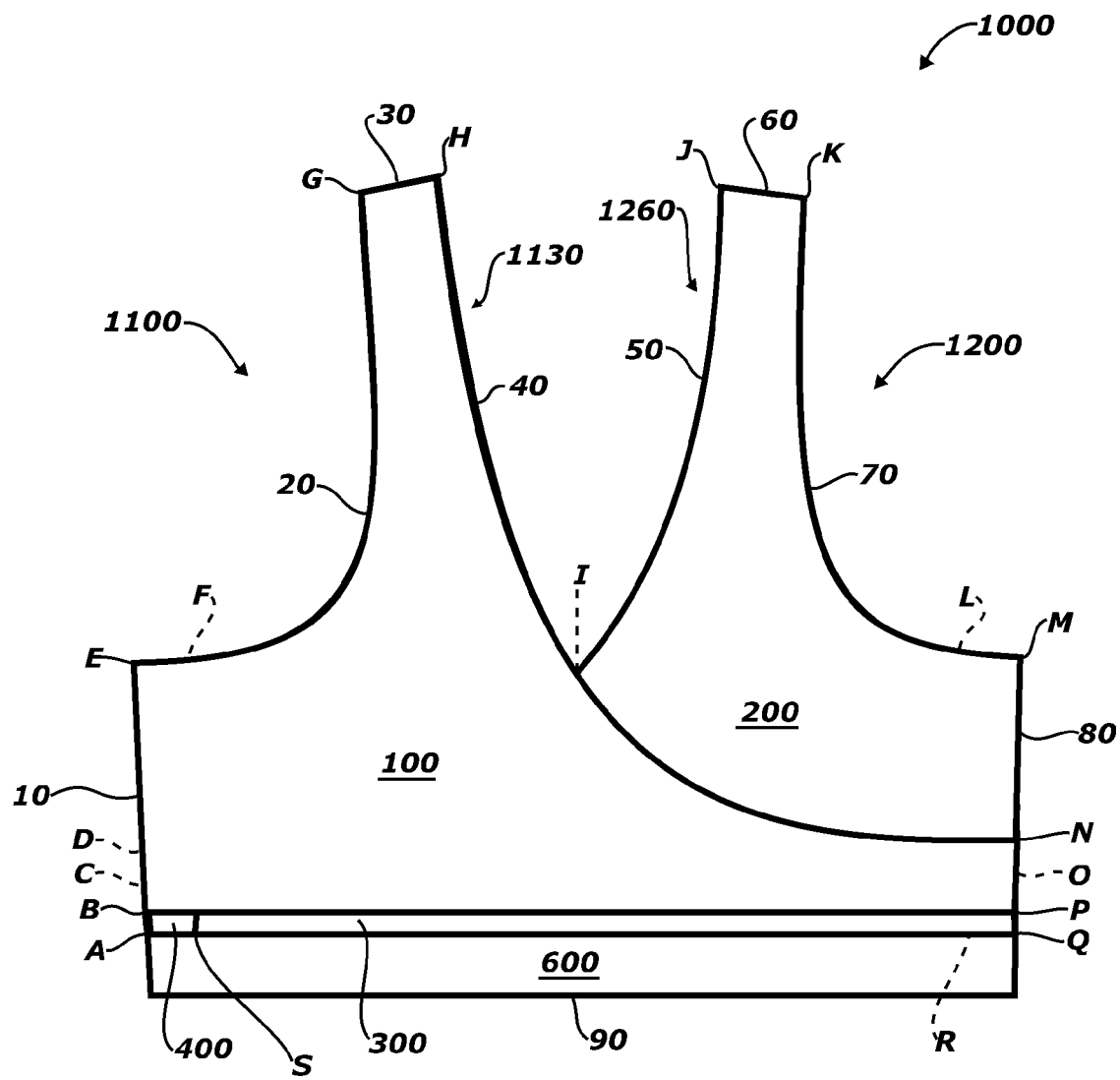
FIG. 1 is a front, elevational illustration of a garment, according to an embodiment of the present disclosure, without a back component, for ease of viewing.

The illustrations presented herein are not meant to be actual views of any particular component, garment, or system, but are merely idealized representations that are employed to describe embodiments of the present disclosure.

As used herein, the terms "right" and "left," when referring to an object, or part thereof, or to a wearer, or part thereof, mean the right and left, respectively, from the perspective of the object or the wearer.

As used herein, the term "lateral" means proximate to a side of a body or an object.

As used herein, the term "medial" means proximate to the median axis of a body or an object.

As used herein, the term "vertical" means a direction substantially parallel to the median axis of a body or an object.

As used herein, the term "disengaged configuration" means and includes a configuration in which components of the garment are positioned in a manner that does not enable engagement of the garment with a breast pump funnel or engagement between a breast and a nursing infant, without moving one or more of the components from the configuration.

As used herein, the term "pumping configuration" means and includes a configuration in which components of the garment are positioned in a manner that enables engagement of the garment with a breast pump funnel. As used herein, the term "right-pumping configuration" means and includes a pumping configuration that enables engagement of a right-chest component of the garment with a breast pump funnel, without moving one or more of the components of the garment from the configuration. As used herein, the term "left-pumping configuration" means and includes a pumping configuration that enables engagement of a left-chest component of the garment with a breast pump funnel, without moving one or more of the components of the garment from the configuration.

As used herein, the term "nursing configuration" means and includes a configuration in which components of the garment are positioned in a manner that enables engagement between a breast and a nursing infant. As used herein, the term "right-nursing configuration" means and includes a nursing configuration that enables engagement between a right breast and a nursing infant, without moving one or more of the components from the configuration. As used herein, the term "left-nursing configuration" means and includes a nursing configuration that enables engagement between a left breast and a nursing infant, without moving one or more of the components from the configuration.

As used herein, the term "free edge," when referring to an edge of an identified component or layer, means an edge, of the identified component or layer, that is not affixed along its length to one or more other objects such that the free edge is configured to be selectively and temporarily moved away from its disengaged configuration without permanently transforming the garment. For example and without limitation, a free edge may include an edge lacking any means to secure its length to the one or more other objects. A free edge may also include an edge configured to be selectively unsecured along its length to the one or more other objects, e.g., by a zipper, a hook-and-loop engagement, or the like.

As used herein, the term "attached edge," when referring to an edge of an identified component or layer, means an edge, of the identified component or layer, that is affixed along its length, in whole or in part, to one or more other objects such that the attached edge cannot be selectively moved away from its disengaged configuration without permanently transforming the garment. For example and without limitation, an attached edge may include an edge stitched in whole or in part to secure its length to the one or more other objects. An attached edge may also include an edge glued or otherwise bonded to secure its length to the one or more other objects.

As used herein, the term "seamless," when referring to a component or layer, means and includes a component or layer lacking stitching substantially interior to a periphery of the component or layer.

As used herein, the term "continuous," when referring to a component or layer, means and includes a component or layer lacking gaps, holes, or other openings defined interior to a periphery of the component or layer.

The following description provides specific details, such as material types and attachment points in order to provide a thorough description of embodiments of the present disclosure. However, a person of ordinary skill in the art will understand that the embodiments of the present disclosure may be practiced without employing these specific details. Indeed, the embodiments of the present disclosure may be practiced in conjunction with conventional garment assembly techniques employed in the industry.

Garments for use by nursing women are disclosed. The garments include layers of material that at least partially overlap one another. The funnel of a breast pump may be received behind free edges of overlapping layers such that the free edges support the funnel from multiple directions. Thus, a funnel may be placed in the garment and supported for hands-free pumping.

Figure 2:
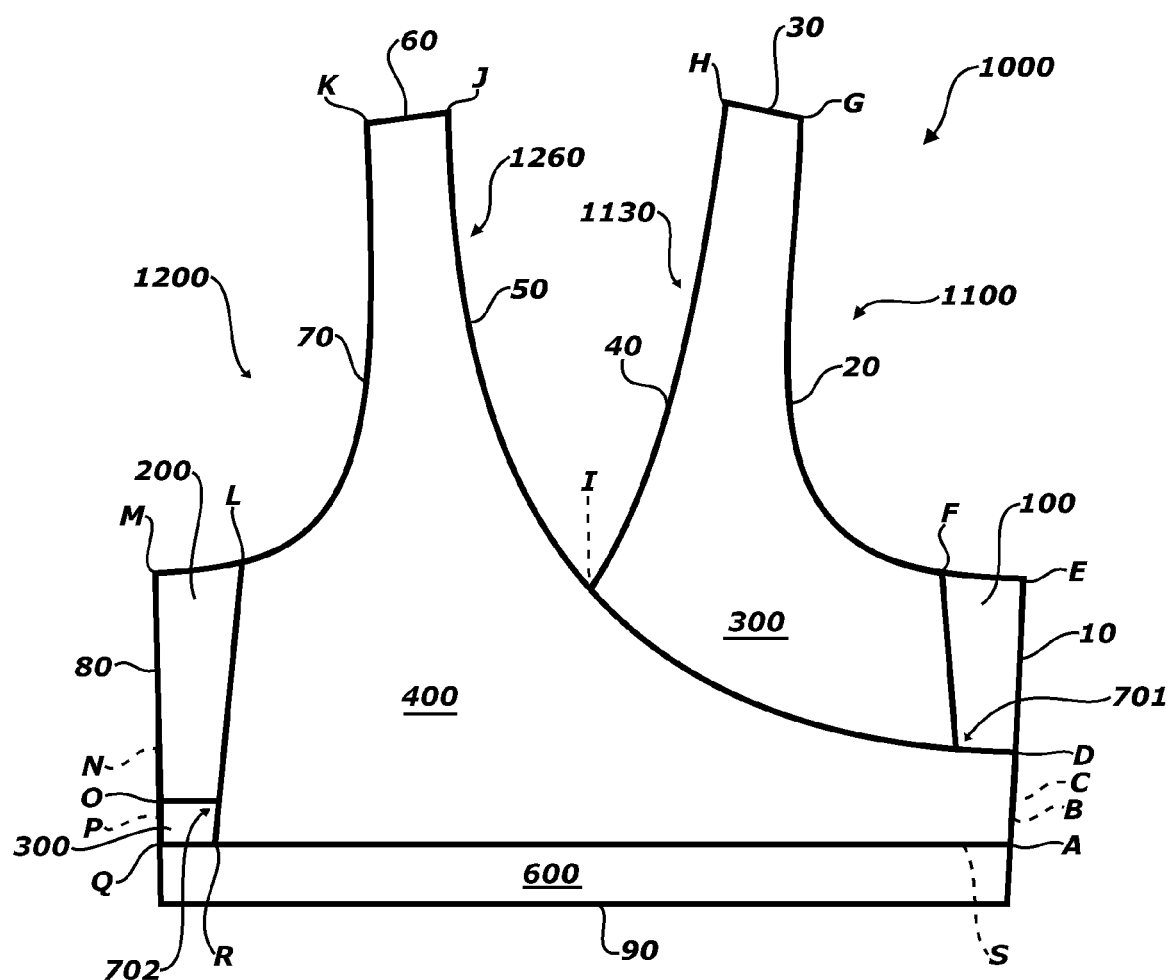
FIG. 2 is a rear, elevation illustration of the garment of FIG. 1, without the back component, for ease of viewing.

FIG. 1 illustrates, from a front view, a garment 1000 configured to enable hands-free pumping. FIG. 2 illustrates the front components of the garment 1000 from a rear view (i.e., illustrates an inside-out view of that illustrated in FIG. 1).

Figure 15:
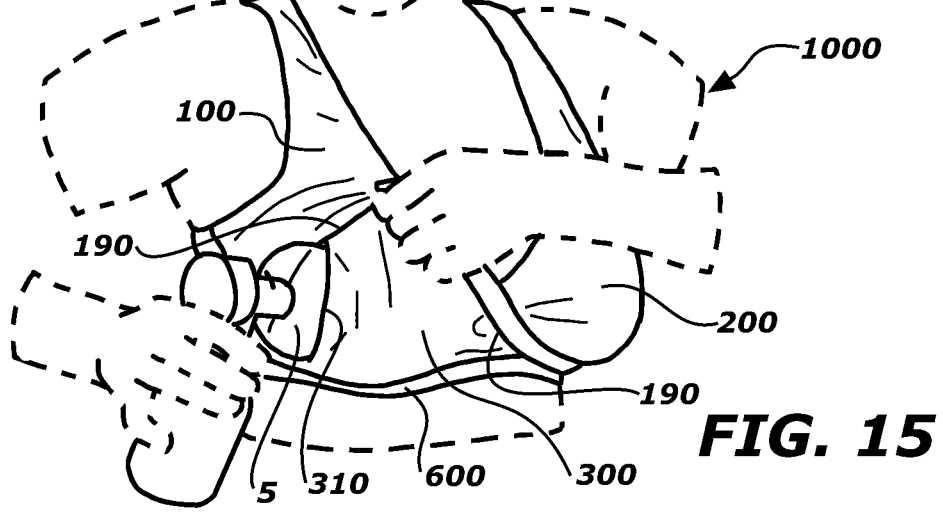

The garment 1000 includes two cups, each provided by one of a right-chest component 1100 and a left-chest component 1200. The garment 1000 is configured to receive and support a funnel 5 (FIG. 15) of a conventional breast pump at any nipple location on a breast. The right-chest component 1100 and the left-chest component 1200 of the garment 1000 include at least one outer and inner layer that are arranged to at least partially overlap one another. The right-chest component 1100 and the left-chest component 1200 are also arranged to cross over each other. Each of the right-chest component 1100 and the left-chest component 1200 includes at least one free edge (e.g., right medial edge 40 and left medial edge 50) that may be transitioned to a pumping configuration in which the free edge supports at least part of the funnel 5 (FIG. 15). Thus, in the pumping configuration, when one or both of the right-chest component 1100 and the left-chest component 1200 selectively receive the funnel 5 (FIG. 15), the free edge, along with additional free or attached edges of the garment 1000 each provide support to the funnel 5 (FIG. 15). Such additional free or attached edges of the garment 1000 may include, for example, edges, of the outer and inner layers of the right-chest component 1100 or the left-chest component 1200, joined together to form another free edge of the garment 1000, which free edge extends from one of a pair of shoulder straps of the garment 1000 to a position underneath an adjacent breast. Therefore, the funnel 5 (FIG. 15) may be supported, during pumping, from multiple (e.g., three) angles or sides defining a triangle-like opening in which the funnel 5 (FIG. 15) may be received and positioned over the nipple to express milk.

The garment 1000 is configured such that, when worn in at least a disengaged configuration (see FIG. 10), outer and inner layers of both the right-chest component 1100 and the left-chest component 1200 each substantially cover (e.g., conceal) a respective breast of the wearer. Each of the outer layers and inner layers include at least one free edge. For example, each outer layer may include a free lower edge, and each inner layer may include a free lateral edge. The free edges enable the funnel 5 (FIG. 15) to be behind the free edges.

The outer and inner layers of one of the right-chest component 1100 and the left-chest component 1200 extend from one cup of the garment 1000 to under the other cup of the garment 1000. Thus, the outer and inner layers of one of the chest components 1100, 1200 may be configured to provide a third layer at least partially overlapping (e.g., overlaying, underlying, laying between) the other and inner layers of the other of the chest components 1100, 1200. This third layer may provide additional support for the funnel 5 (FIG. 15) of the breast pump when the garment 1000 is used in a pumping configuration (see, e.g., FIGS. 18 and 23). More particularly, the additional support from the third layer may be provided by a free edge of one of the components 1100, 1200 of the garment 1000. The free edge may be formed by joining medial edges of each of the outer and inner layers of the component 1100, 1200. The free edge extends from a shoulder strap above one cup of the garment 1000 to a lower portion of another cup of the garment 1000. The free edge of a first one of the components 1100, 1200 may overlay the outer and inner layers of the a second one of the components 1100, 1200, while the free edge of the second of the components 1100, 1200 may underlay the outer and inner layers of the first of the components 1100, 1200. Thus, the components 1100, 1200 may be disposed to cross one another (e.g., crisscrossing) over the chest.

With continued reference to FIG. 1, visible from the front exterior of the garment 1000 are a right outer layer 100, a portion of a left outer layer 200, and a front side of a rib band 600. The right outer layer 100 may be a seamless, continuous outer material layer of the right-chest component 1100 and may cover the right breast of a wearer. The left outer layer 200 may be a seamless, continuous outer material layer of the left-chest component 1200 and may cover the left breast of the wearer.

FIGS. 1 and 2 also illustrate sides and edges of the garment 1000, namely, a right lateral side 10, an upper right lateral edge 20, a right shoulder side 30, a right medial edge 40, a left medial edge 50, a left shoulder side 60, a left upper lateral edge 70, a left lateral side 80, and a lower edge 90. FIGS. 1 and 2 also show various points, A through S, along the sides and edges of the garment 1000 or components thereof, which points are referenced to provide an understanding of the relative dispositions of the components of the garment 1000. As defined in FIGS. 1 and 2, the right lateral side 10 of the garment 1000 includes points A through E; the upper right lateral edge 20 includes points E through G; the right shoulder side 30 includes points G and H; the right medial edge 40 includes points H, I and N; the left medial edge 50 includes points D, I, and J; the left shoulder side 60 includes points J and K, the left upper lateral edge 70 includes points K through M; the left lateral side 80 includes points M through Q; and the lower edge 90 passes proximate to points Q through S and A. The rib band 600 may be connected, in the garment 1000, along the lower edge 90.

Point I identifies the medial centerline of the garment 1000, and the right medial edge 40 may cross over the left medial edge 50 approximately at point I. In some embodiments, the right medial edge 40 may not be directly connected to the left-chest component 1200 or the left outer layer 200, except along the left lateral side 80 of the garment 1000. Likewise, in such embodiments, the left medial edge 50 may not be directly connected to the right-chest component 1100 or the right outer layer 100, except along the right lateral side 10 of the garment 1000. Therefore, the right medial edge 40 and the left medial edge 50 may each be free edges of the garment 1000.

The garment 1000 includes a pair of shoulder straps, i.e., a right shoulder strap 1130 and a left shoulder strap 1260. The right outer layer 100 extends between one of the shoulder straps, e.g., the right shoulder strap 1130, and each of the lateral edges of the garment 1000 (i.e., the right lateral side 10 and the left lateral side 80). The left outer layer 200 extends between the other of the shoulder straps, e.g., the left shoulder strap 1260, and each of the lateral edges of the garment 1000 (i.e., the right lateral side 10 and the left lateral side 80).

With reference to FIG. 2, the inside of the garment 1000 shows a right inner layer 300 of the right-chest component 1100 and a left inner layer 400 of the left-chest component 1200. The right inner layer 300 may be a seamless, continuous material layer that covers the right breast of the wearer. The left inner layer 400 may be a seamless, continuous material layer that covers the left breast of the wearer. The left inner layer 400 may be fully visible from the inside view, while the right inner layer 300 may be only partially visible due to the overlap between the right-chest component 1100 and the left-chest component 1200. Though, the garment 1000, illustrated in FIGS. 1 and 2 includes the right-chest component 1100, with both its right outer layer 100 and right inner layer 300, overlaying the left-chest component 1200, with both its left outer layer 200 and left inner layer 400, in other embodiments, the layers of the left-chest component 1200 may overlay the layers of the right-chest component 1100.

Each of the inner layers, i.e., the right inner layer 300 and the left inner layer 400, extend from an opposite lateral side of the garment 1000 to a point that is medially disposed relative to the other lateral side of the garment 1000. For example, the right inner layer 300 extends from the left lateral side 80 of the garment 1000 to a point, e.g., points F and S, medially disposed relative to the right lateral side 10 of the garment 1000. On the other hand, the left inner layer 400 extends from the right lateral side 10 of the garment 1000 to a point, e.g., points L and R, medially disposed relative to the left lateral side 80 of the garment 1000. Therefore, the inner layers 300, 400 underlay the outer layers 100, 200, respectively, in such a manner that an edge of each of the inner layers 300, 400 crosses over an edge of each of the outer layers 100, 200, respectively, to define, at the intersections a right nook 701 and a left nook 702, respectively. In the disengaged configuration (e.g., FIG. 2), the right nook 701, formed by a lateral edge of the right inner layer 300 and the left medial edge 50 of the left-chest component 1200, is covered by the right outer layer 100 of the right-chest component 1100. Also, in the disengaged configuration (e.g., FIG. 2), the left nook 702, formed by a lateral edge of the left inner layer 400 and the right medial edge 40 of the right-chest component 1100, is covered by the right inner layer 300 of the right-chest component 1100. In a pumping configuration (see, e.g., FIGS. 18 and 23), the funnel 5 (FIG. 15) of a breast pump may be received in one of the nooks 701, 702 and supported therein by the edges that define nooks 701, 702 in addition to by another edge of the garment 1000, as described further below.

Figure 3:
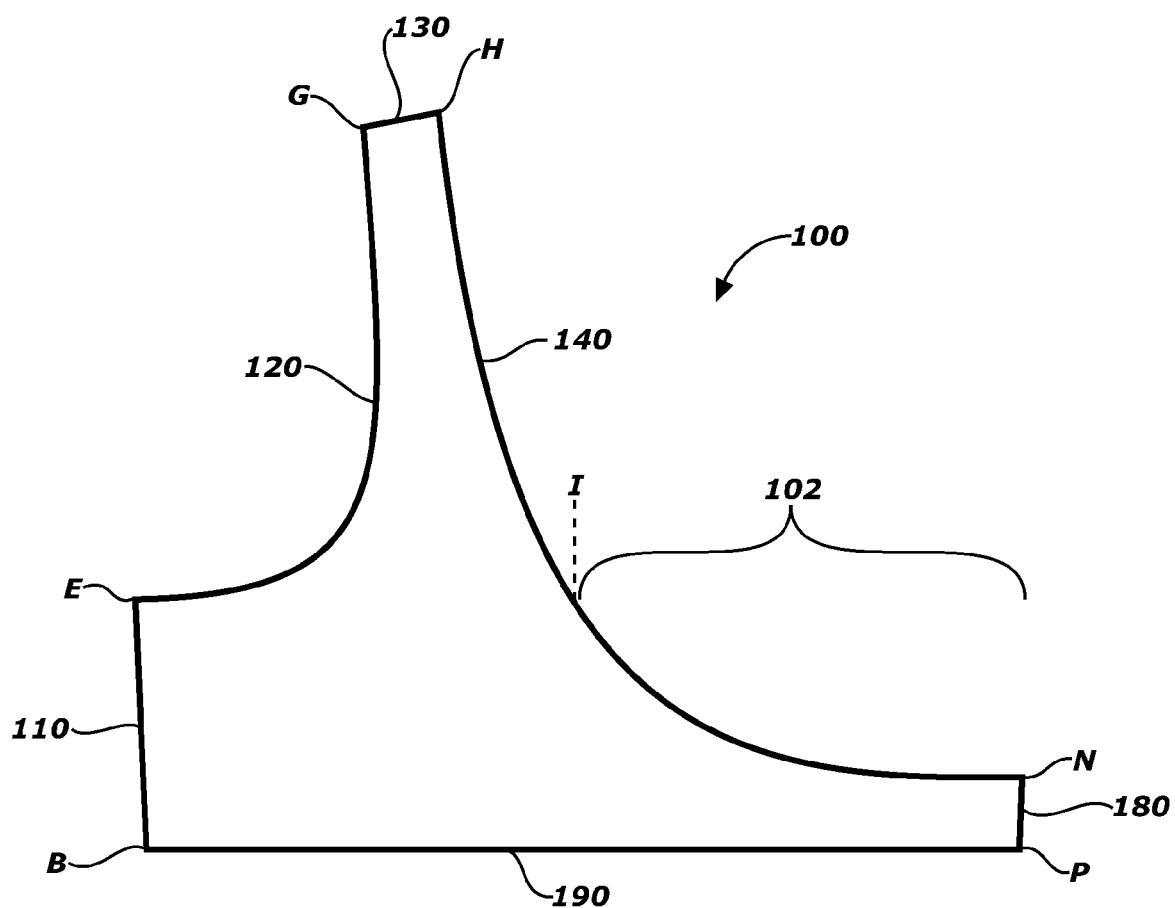
FIG. 3 is a front, elevational illustration of an outer material layer of a right-chest component of the garment of FIG. 1.

With reference to FIG. 3, illustrated is a front view of the right outer layer 100. The right outer layer 100 includes a right lateral edge 110 that extends between points B and E, an upper right lateral edge 120 that extends between points E and G, a right shoulder edge 130 that extends between points G and H, a medial edge 140 that extends between points H and N while crossing the medial centerline (point I), a left lateral edge 180 that extends between points N and P, and a lower edge 190 that extends between points P and B. A portion of the right outer layer 100 to the left side of the medial centerline (point I), is an extension 102 that extends under the left breast of the wearer. Therefore, the extension 102 provides additional support for the left breast and for the funnel 5 (FIG. 15) engaged with the left breast when the garment 1000 is in a left-pumping configuration (see FIG. 23).

Figure 18:
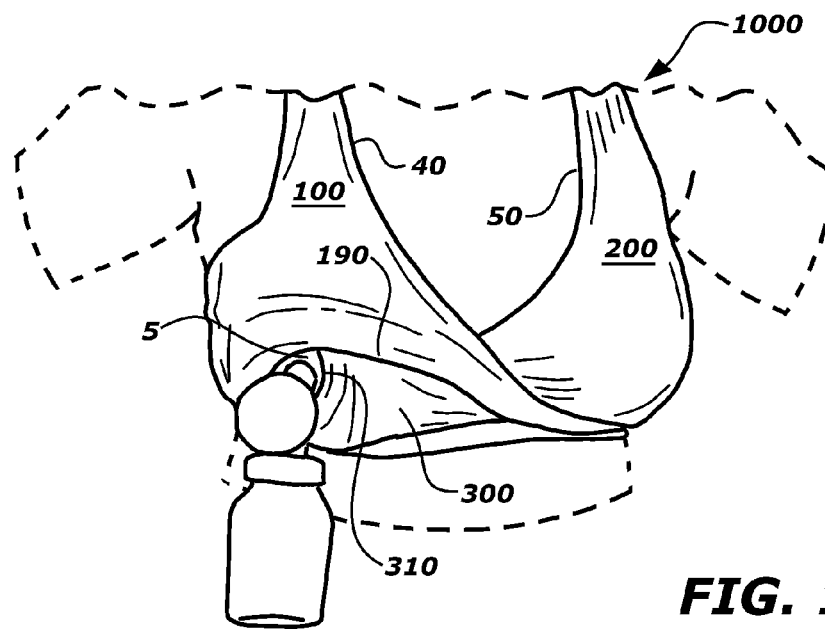
FIG. 18 is a front, elevational, perspective, partial illustration of the garment of FIG. 10, in the right-pumping configuration.

In the constructed garment 1000, the lower edge 190 of the right outer layer 100 provides a free edge behind which the funnel 5 (FIG. 15) may be received in a right-pumping configuration (see FIG. 18). Also, in the constructed garment 1000, the medial edge 140 of the right outer layer 100 may be attached to a medial edge of the right inner layer 300, and, together, the joined medial edges provide a free edge of the right-chest component 1100 (FIG. 1) behind which, in the region of the extension 102, the funnel 5 (FIG. 15) may be received in a left-pumping configuration (see FIG. 23).

Figure 4:
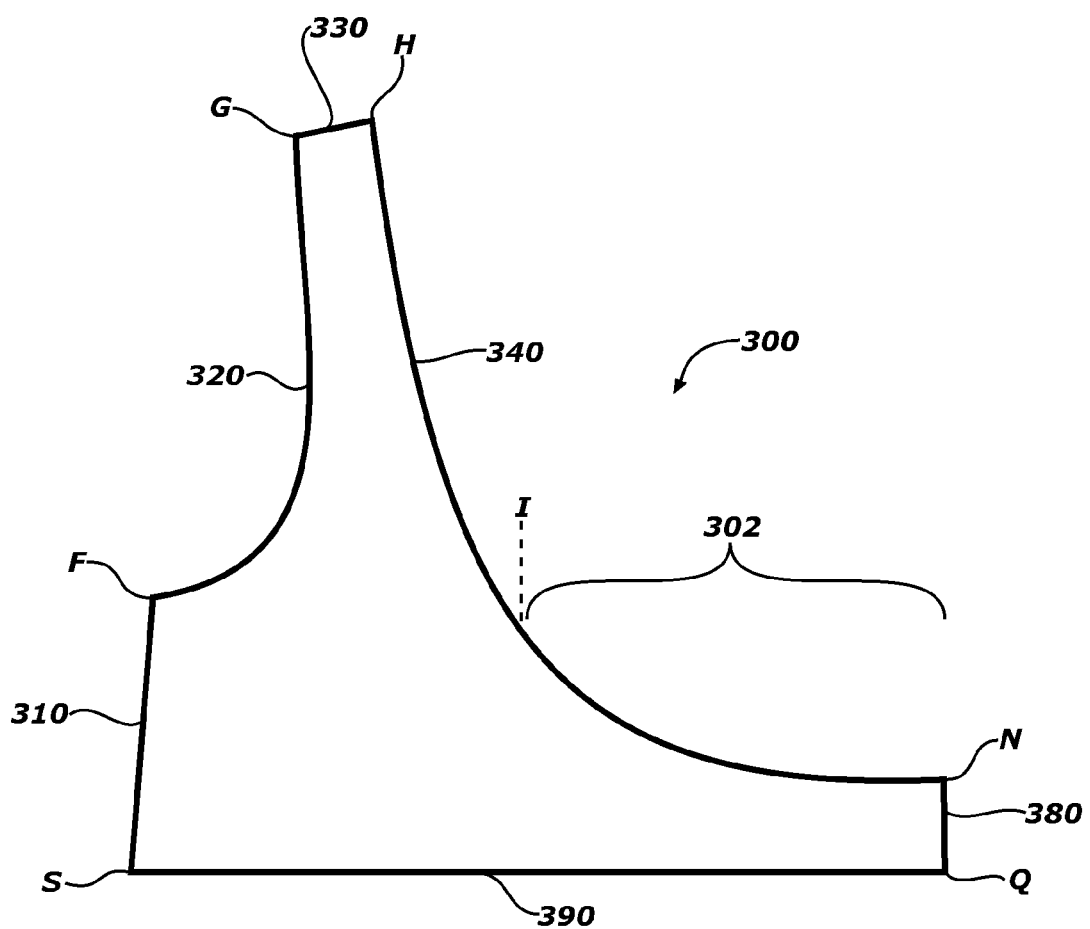
FIG. 4 is a front, elevational illustration of an inner material layer of the right-chest component of the garment of FIG. 1.

With reference to FIG. 4, illustrated is a front view of the right inner layer 300. The right inner layer 300 includes a right lateral edge 310 that extends between points S and F, an upper right lateral edge 320 that extends between points F and G, a right shoulder edge 330 that extends between points G and H, a medial edge that extends between points H and N while crossing over the medial centerline (point I), a left lateral edge 380 that extends between points N and Q, and a lower edge 390 that extends between points Q and S. A portion of the right inner layer 300 to the left side of the medial centerline (point I) is an extension 302 that, with extension 102 (FIG. 3) of the right outer layer 100 (FIG. 3), extends under the left breast of the wearer. Therefore, the extension 302 provides additional support for the left breast and for the funnel 5 (FIG. 15) engaged with the left breast when the garment 1000 is in a left-pumping configuration (see FIG. 23).

In the constructed garment 1000, the right lateral edge 310, which may be substantially vertical, provides a free edge behind which the funnel 5 (FIG. 15) may be received in the right-pumping configuration (see FIG. 18). Also, in the constructed garment 1000, a medial edge 340 of the right inner layer 300 may be attached to the medial edge 140 of the right outer layer 100 and together provide a free edge of the right-chest component 1100 (FIG. 1) behind which, in the region of the extension 302, the funnel 5 (FIG. 15) may be received in the left-pumping configuration (see FIG. 23).

Figure 5:
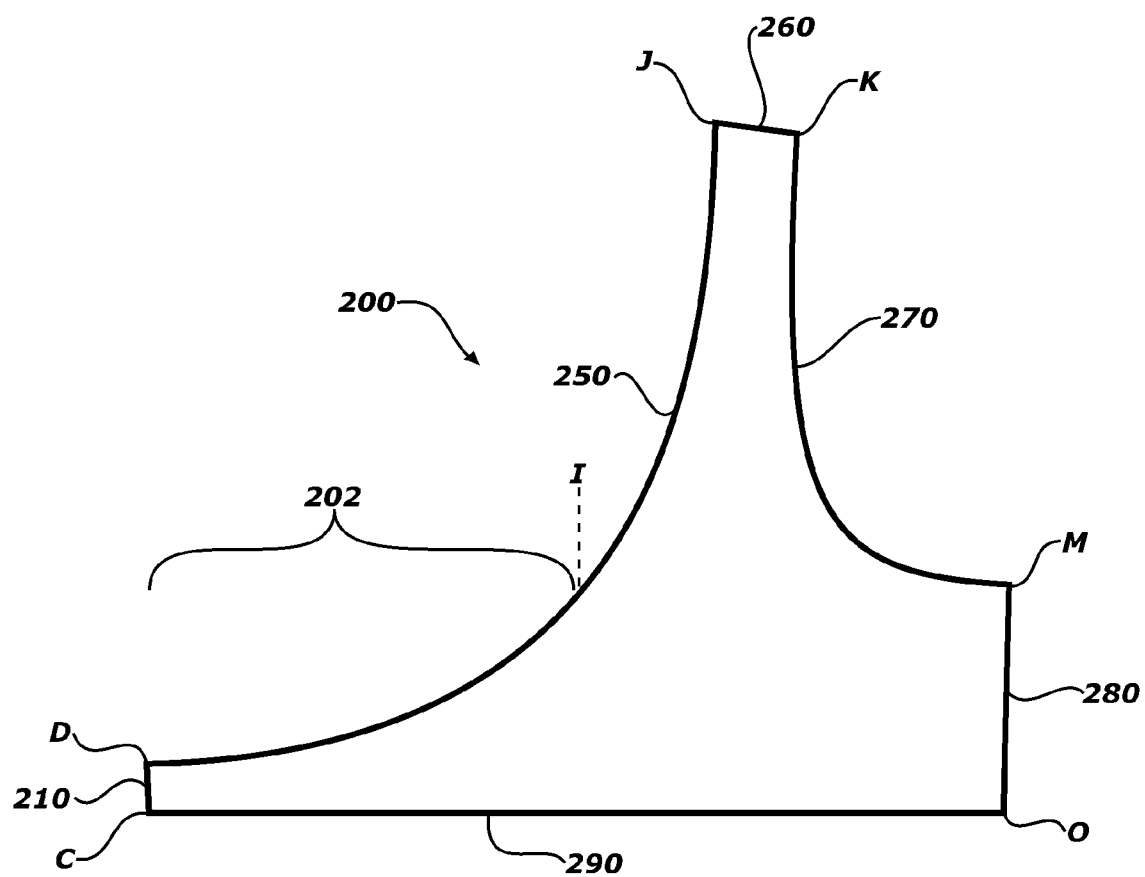
FIG. 5 is a front, elevational illustration of an outer material layer of a left-chest component of the garment of FIG. 1.

With reference to FIG. 5, illustrated is a front view of the left outer layer 200. The left outer layer 200 includes a right lateral edge 210 extending between points C and D, a medial edge 250 extending between points D and J while crossing through the medial centerline (point I), a left shoulder edge 260 extending between points J and K, an upper left lateral edge 270 extending between points K and M, a left lateral edge 280 extending between points M and O, and a lower edge 290 extending between points O and C. A portion of the left outer layer 200 to the right side of the medial centerline (point I) is an extension 202 that extends under the right breast of the wearer. Therefore, the extension 202 provides additional support for the right breast and for the funnel 5 (FIG.

15) engaged with the right breast when the garment 1000 is in a right-pumping configuration (see FIG. 18).

Figure 23:
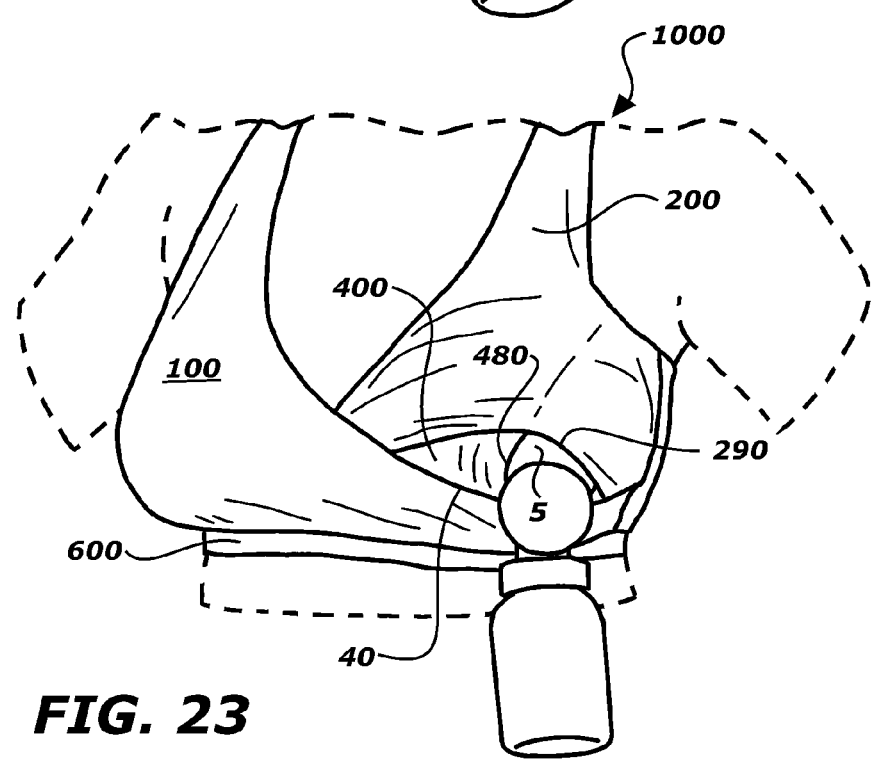
FIG. 23 is a front and left-side, elevational, perspective, partial illustration of the garment of FIG. 10, in the left-pumping configuration.

In the constructed garment 1000, the lower edge 290 of the left outer layer 200 provides a free edge behind which the funnel 5 (FIG. 15) may be received in a left-pumping configuration (see FIG. 23). Also, in the constructed garment 1000, the medial edge 250 of the left outer layer 200 may be attached to a medial edge of the left inner layer 400, and, together, the joined medial edges provides a free edge of the left-chest component 1200 (FIG. 1) behind which, in the region of the extension 202, the funnel 5 (FIG. 15) may be received in a right-pumping configuration (see FIG. 18).

Figure 6:
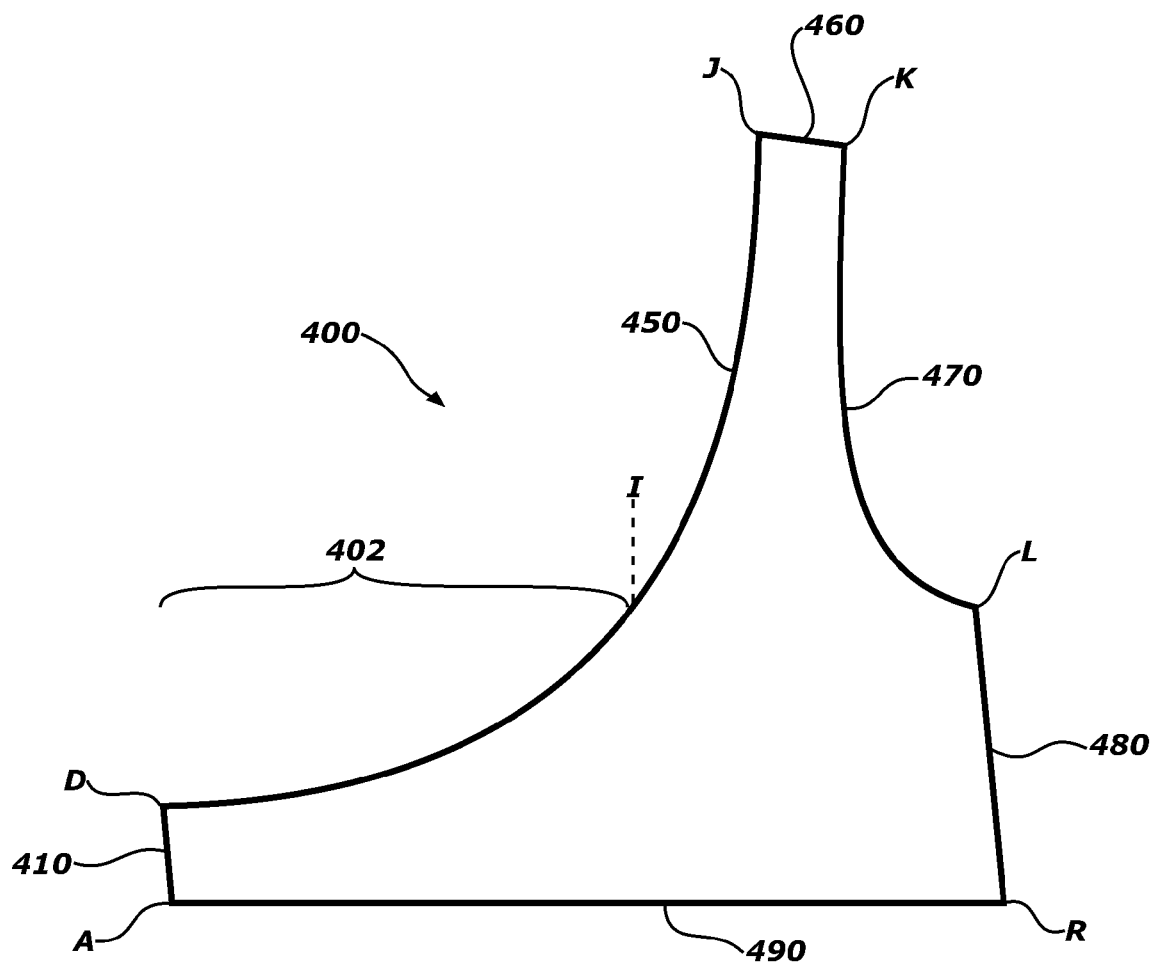
FIG. 6 is a front, elevational illustration of an inner material layer of the left-chest component of the garment of FIG. 1.

With reference to FIG. 6, illustrated is a front view of the left inner layer 400. The left inner layer 400 includes a right lateral edge 410 extending between points A and D, a medial edge 450 extending between points D and J while crossing through the medial centerline (point I), a left shoulder edge 460 extending between points J and K, an upper left lateral edge 470 extending between points K and L, a left lateral edge 480 extending between points L and R, and a lower edge 490 extending between points R and A. A portion of the left inner layer 400 to the right side of the medial centerline (point I) is an extension 402 that, with extension 202 (FIG. 5) of the left outer layer 200 (FIG. 5), extends under the right breast of the wearer. Therefore, the extension 402 provides additional support for the right breast and for the funnel 5 (FIG. 15) engaged with the right breast when the garment 1000 is in a right-pumping configuration (see FIG. 18).

In the constructed garment 1000, the left lateral edge 480, which may be substantially vertical, provides a free edge behind which the funnel 5 (FIG. 15) may be received in the left-pumping configuration (see FIG. 23). Also, in the constructed garment 1000, the medial edge 450 of the left inner layer 400 may be attached to the medial edge 250 of the left outer layer 200 and together provide a free edge of the left-chest component 1200 (FIG. 1), behind which, in the region of the extension 402, the funnel 5 (FIG. 15) may be received in the right-pumping configuration (see FIG. 18).

Figure 7:
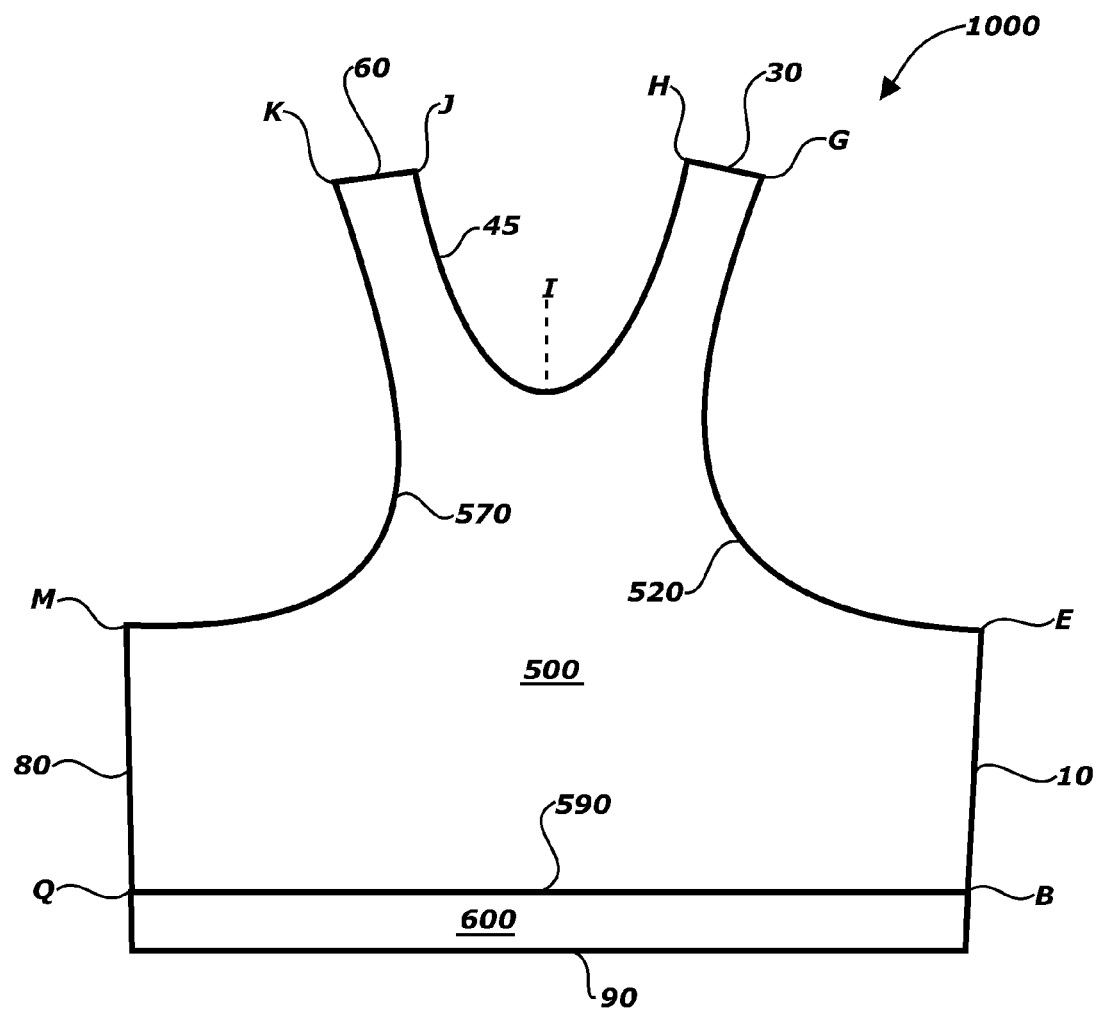
FIG. 7 is a rear, elevational illustration of a back component of a garment, according to an embodiment of the present disclosure.

With reference to FIG. 7, illustrated is a rear view of a back component 500 of the garment 1000, with the rib band 600 attached. In some embodiments, the back component 500 may be a seamless, continuous material piece that extends between sides and edges of the garment 1000, e.g., between the right lateral side 10 and the left lateral side 80 of the garment 1000 and between the right shoulder side 30, the left shoulder side 60, and down proximate to the lower edge 90 of the garment 1000. The back component 500 may be attached to the rib band 600 along a lower edge 590 of the back component. The back component 500 may include an upper left lateral edge 570 extending between points M and K and may include an upper right lateral edge 520 extending between points G and E. The back component 500 may further define a neck edge 45 extending between points J and H while crossing through the medial centerline (point I).

FIGS. 8A through 8J illustrate, in front view, the various components of the garment 1000 in their relative dispositions, from back to front. Therefore, in some embodiments, the various components and layers of the garment 1000 may be overlain, one on another, in the order illustrated in FIGS. 8A through 8J.

Figure 8A:
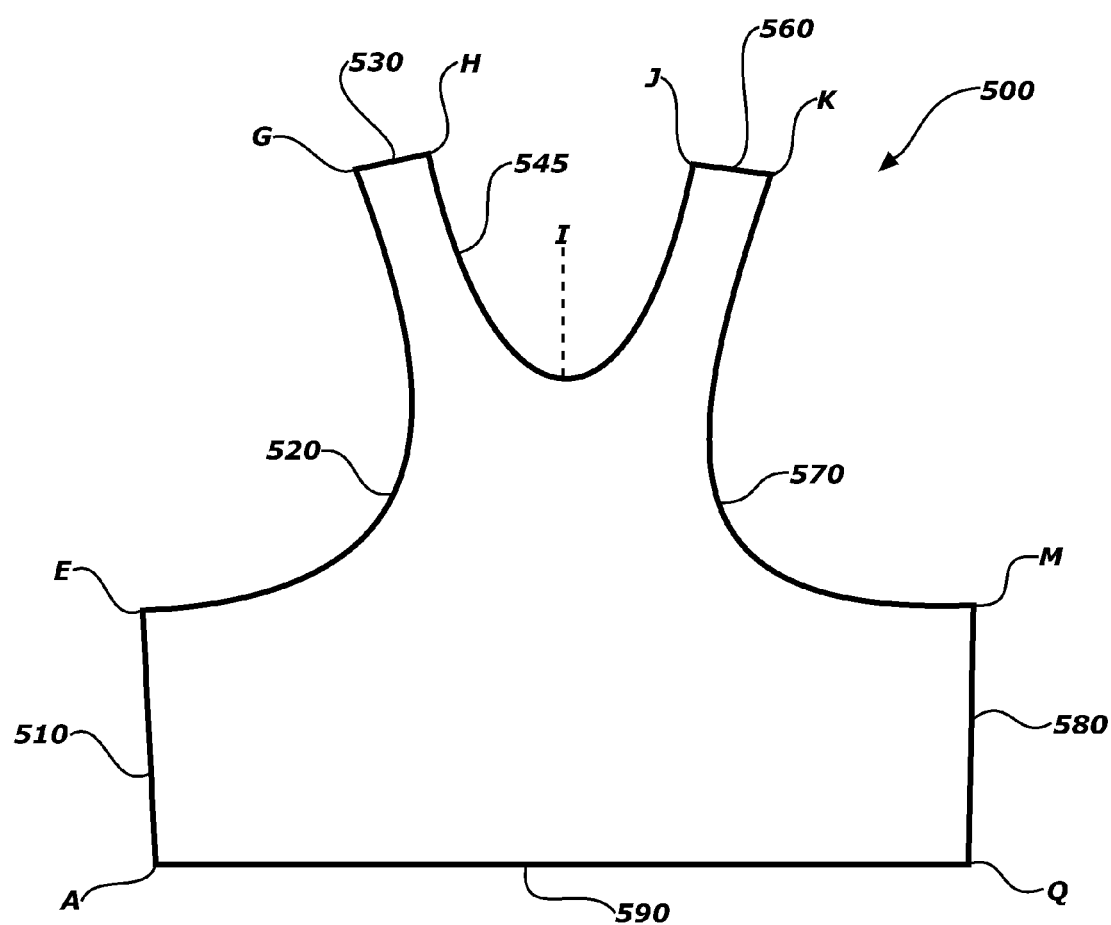
FIGS. 8A through 8J are front, elevational illustrations of various components of the garment of FIG. 1, illustrated in order from back of the garment to front of the garment.

With reference to FIG. 8A, illustrated is a front view of the back component 500, with its right lateral edge 510 extending between points A and E, the upper right lateral edge 520 extending between points E and G, its right shoulder edge 530 extending between points G and H, a neck edge 545 extending between points H and J, its left shoulder edge 560 extending between points J and K, the upper left lateral edge 570 extending between points K and M, its left lateral edge 580 extending between points M and Q, and the lower edge 590 extending between points Q and A.

Figure 8B:
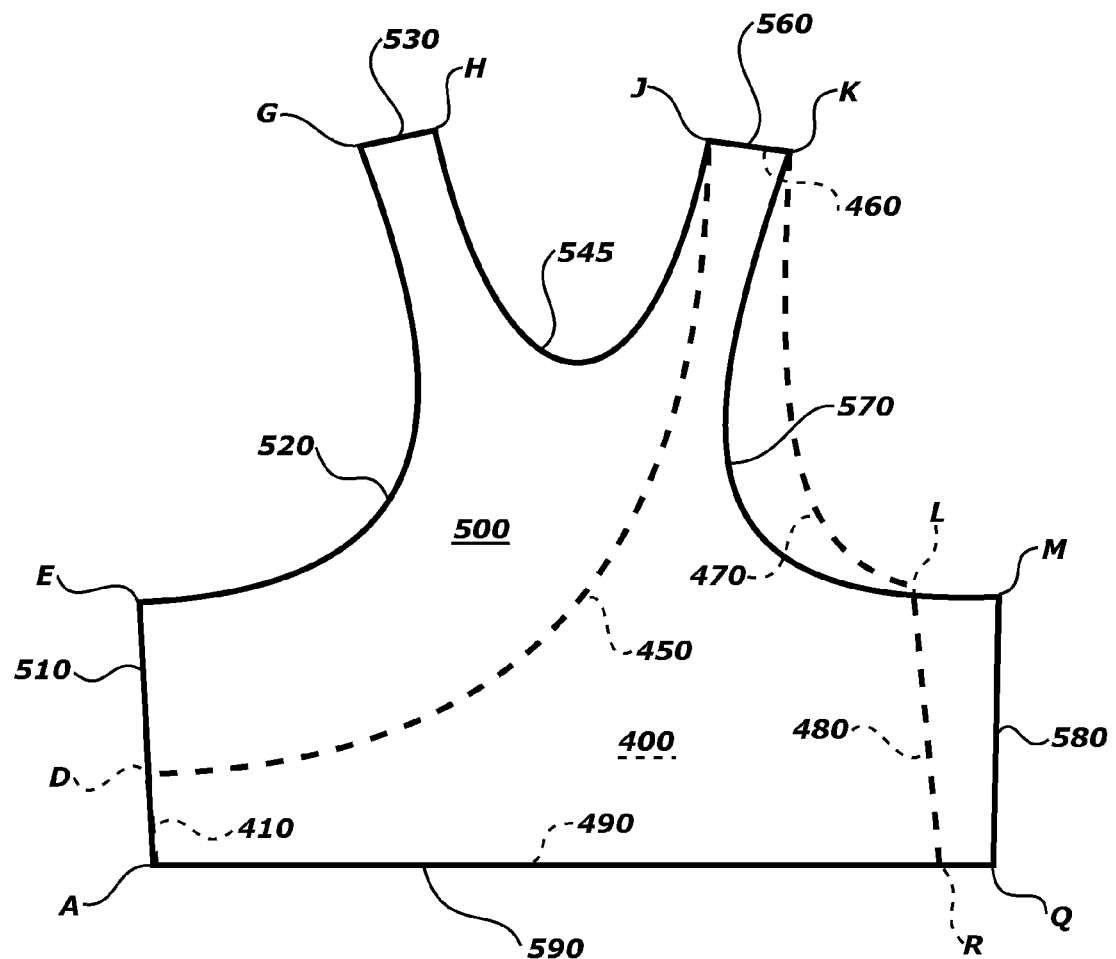

With reference to FIG. 8B, in the constructed garment 1000 (FIG. 1), the left inner layer 400 of the left-chest component 1200 (FIG. 1) may overlay the back component 500. The left shoulder edge 460 of the left inner layer 400 may be adjoined to the left shoulder edge 560 of the back component 500, and the right lateral edge 410 of the left inner layer 400 may be adjoined to a portion of the right lateral edge 510 of the back component 500. As used herein, the term "adjoined," means and includes stitching, bonding, or other substantially permanent attachment along a length of a component or layer.

Figure 8C:
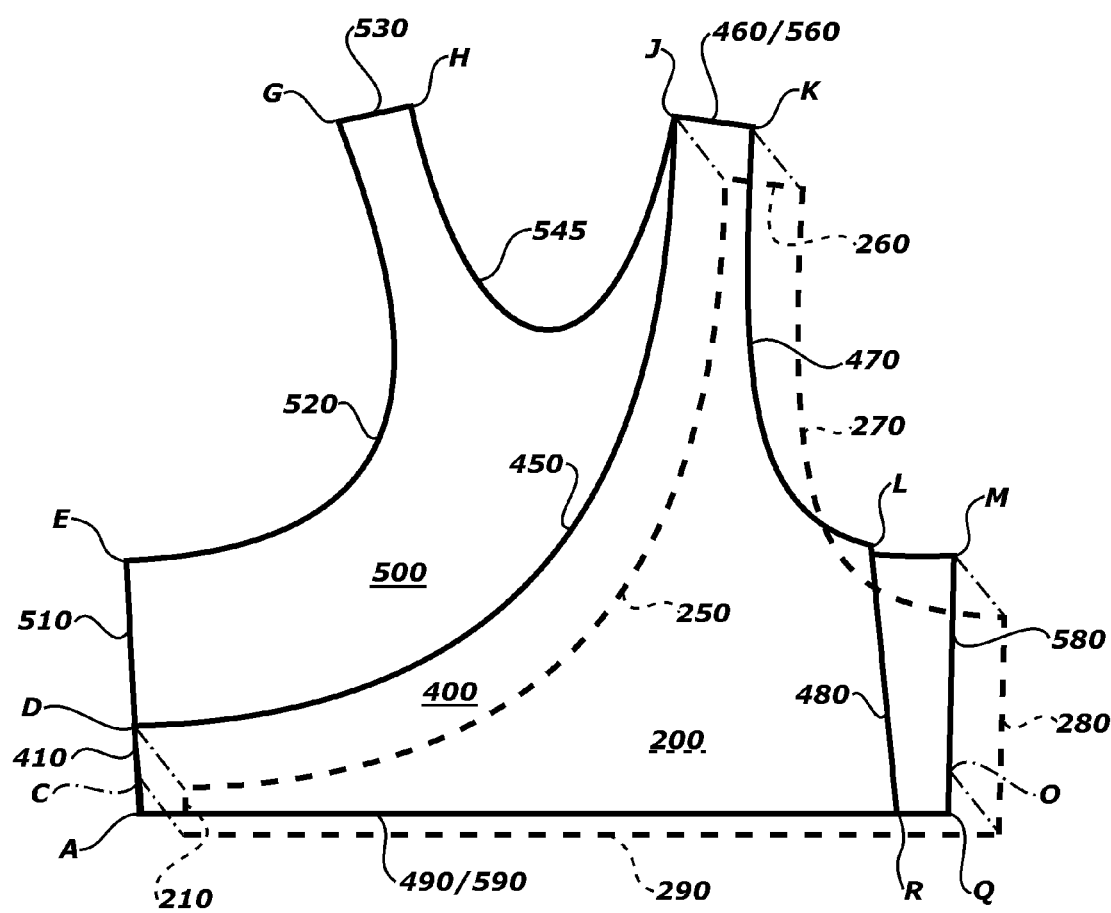
Figure 8D:
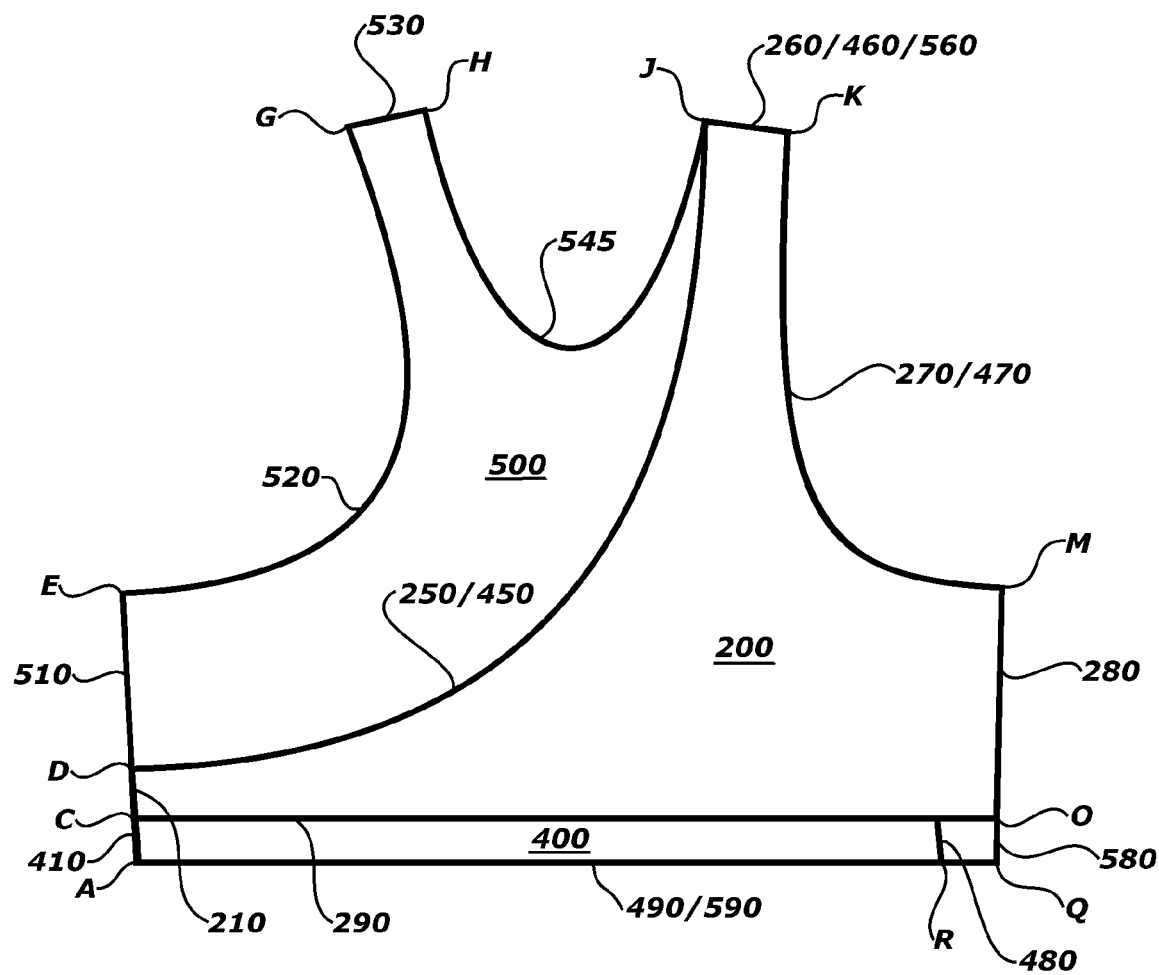

With reference to FIG. 8C, the left outer layer 200 of the left-chest component 1200 (FIG. 1) may overlay the left inner layer 400 and the back component 500. The right lateral edges 210, 410, and 510 may be adjoined to one another, the medial edges 250, 450 may be adjoined to one another, the left shoulder edges 260, 460, 560 may be adjoined to one another, and the upper left lateral edges 270, 470 may be adjoined to one another. With additional reference to FIG. 8D, the joined components and layers leave the left lateral edge 480 of the left inner layer 400 and the lower edge 290 of the left outer layer as free edges. Furthermore, the joined medial edges 250, 450 form a free edge of the left-chest component 1200 (FIG. 1).

Figure 8E:
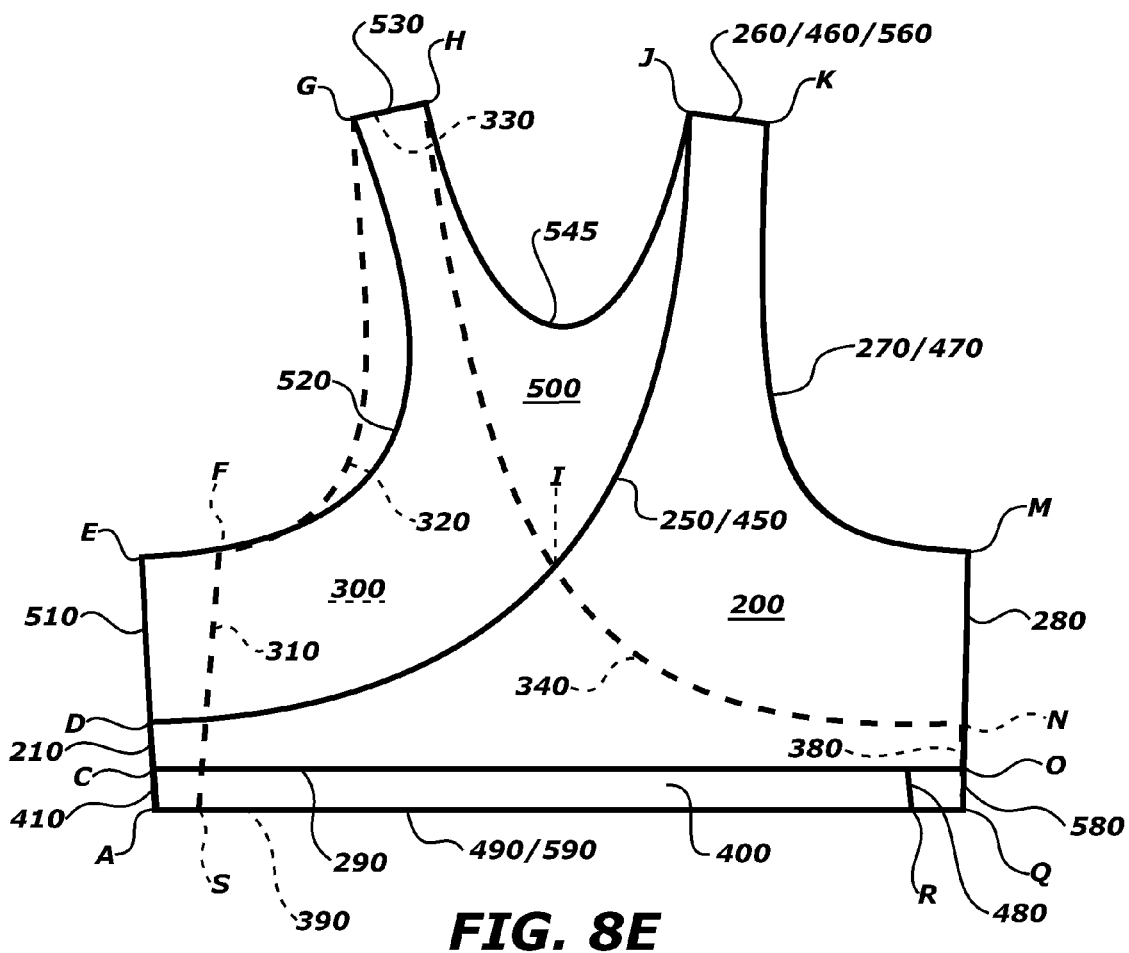
Figure 8F:
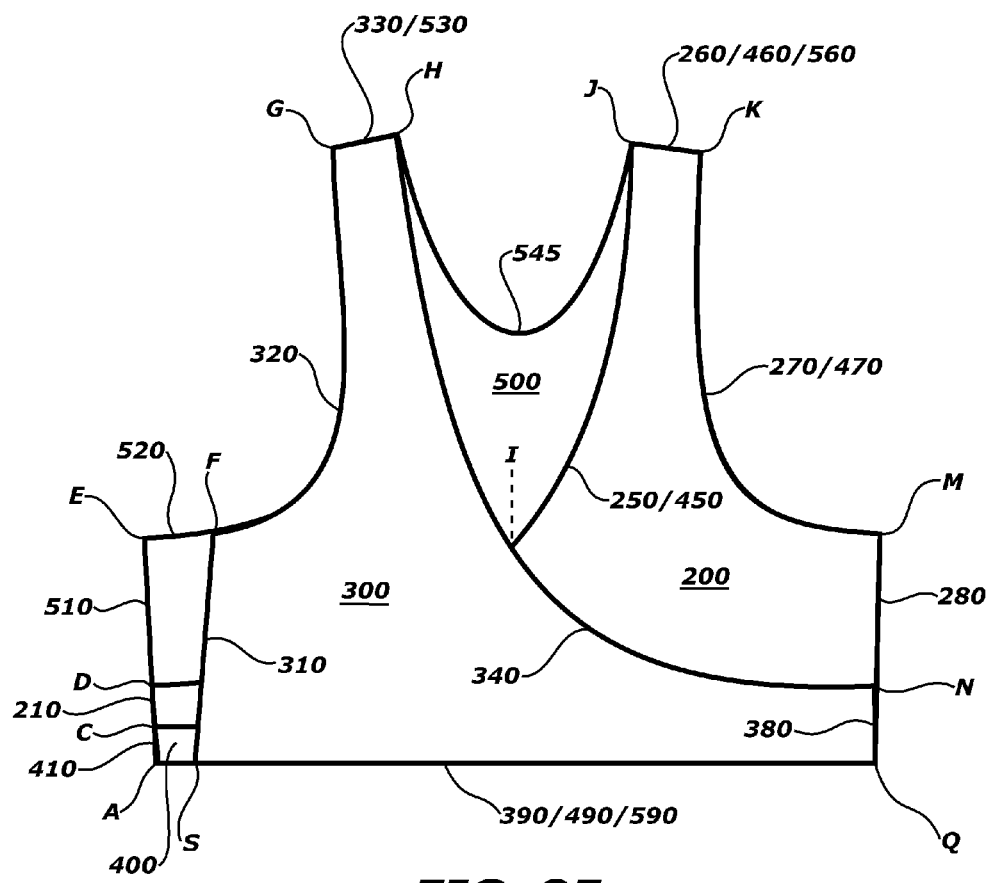

With reference to FIG. 8E, the right inner layer 300 of the right-chest component 1100 (FIG. 1) may overlay the left outer layer 200, the left inner layer 400, and the back component 500. The right shoulder edges 330, 530 may be adjoined to one another, the left lateral edges 380, 280, 580 may be adjoined to one another, and the lower edges 390, 490 of the inner layers (i.e., the right inner layer 300 and the left inner layer 400) may be adjoined to one another. With additional reference to FIG. 8F, the joined components and layers leave the right lateral edge 310 of the right inner layer 300 as a free edge.

Figure 8G:
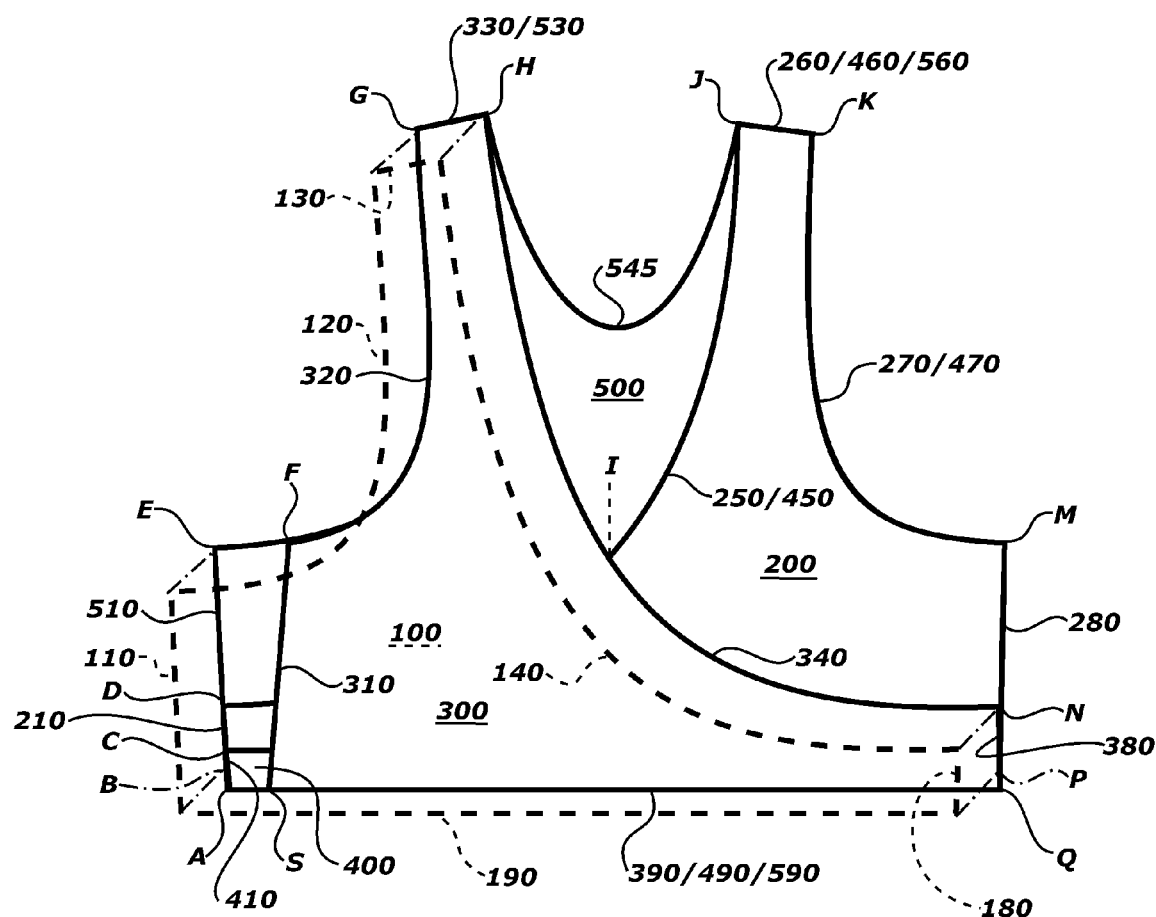
Figure 8H:
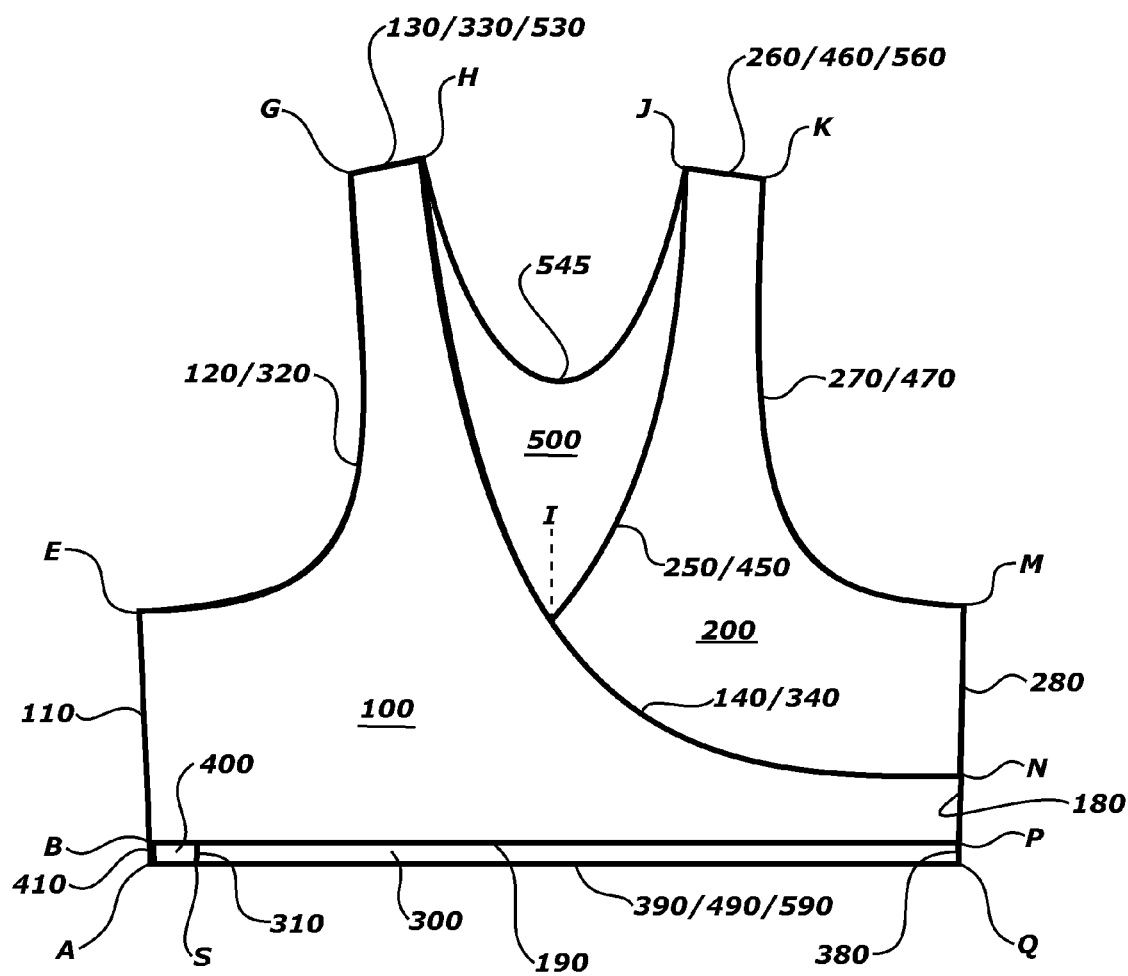

With reference to FIG. 8G, the right outer layer 100 of the right-chest component 1100 (FIG. 1) may overlay the right inner layer 300, the left outer layer 200, the left inner layer 400, and the back component 500. The right lateral edges 110, 210, 410, 510 may be adjoined to one another, the upper right lateral edges 120, 320 may be adjoined to one another, the right shoulder edges 130, 330, 530 may be adjoined to one another, the medial edges 140, 340 may be adjoined to one another, and the left lateral edges 180, 280, 380 may be adjoined to one another. With additional reference to FIG. 8H, the joined components and layers leave the lower edge 190 of the right outer layer 100 as a free edge. Furthermore, the joined medial edges 140, 340 form a free edge of the right-chest component 1100 (FIG. 1).

Figure 8I:
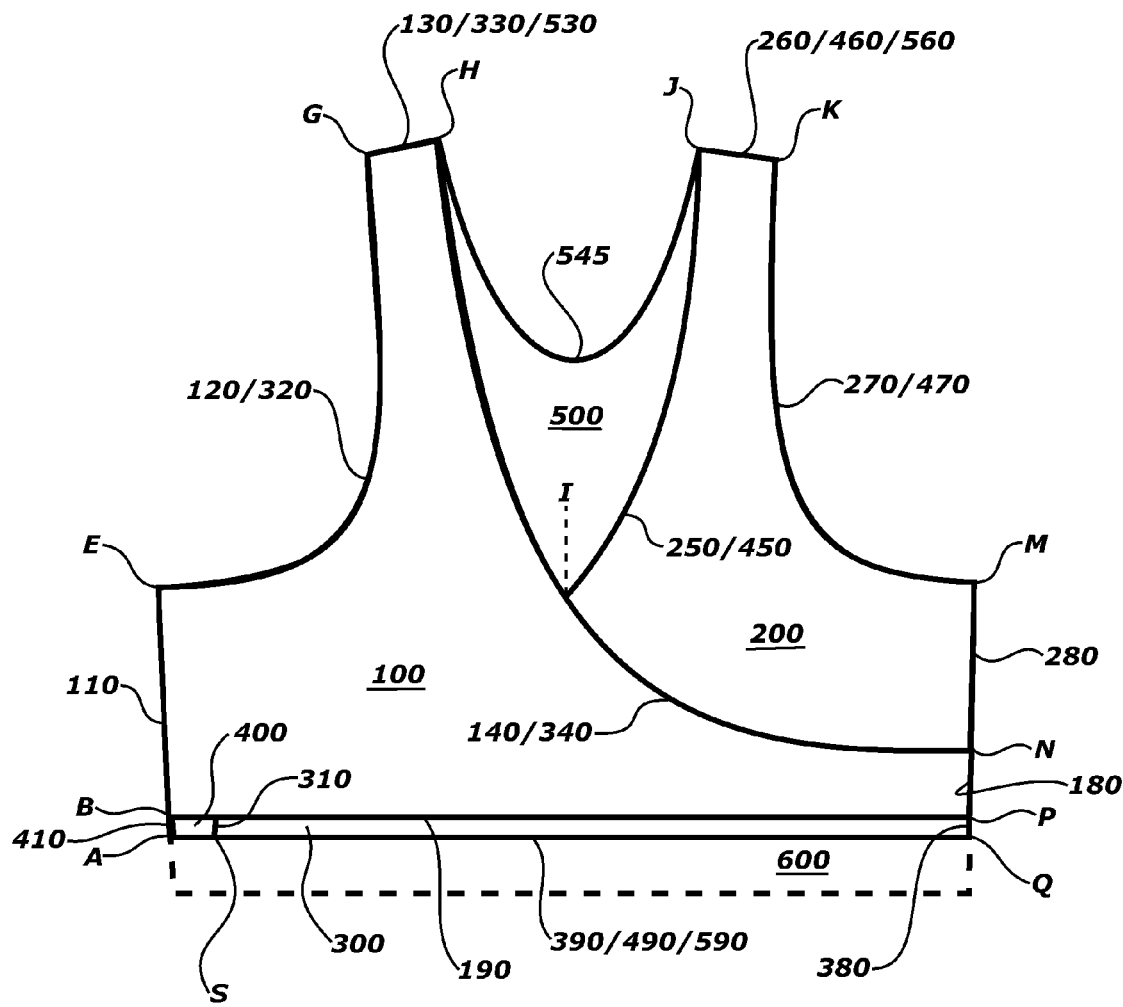

With reference to FIG. 8I, the rib band 600 may be adjoined to the lower edges 390, 490 of the inner layers (i.e., the right inner layer 300 and the left inner layer 400), in the front of the garment 1000, and may be adjoined to the lower edge 590 of the back component 500, in the back of the garment 1000. Therefore, the rib band 600 may border the entire lower edge 90 (FIG. 1) of the garment 1000.

Figure 8J:
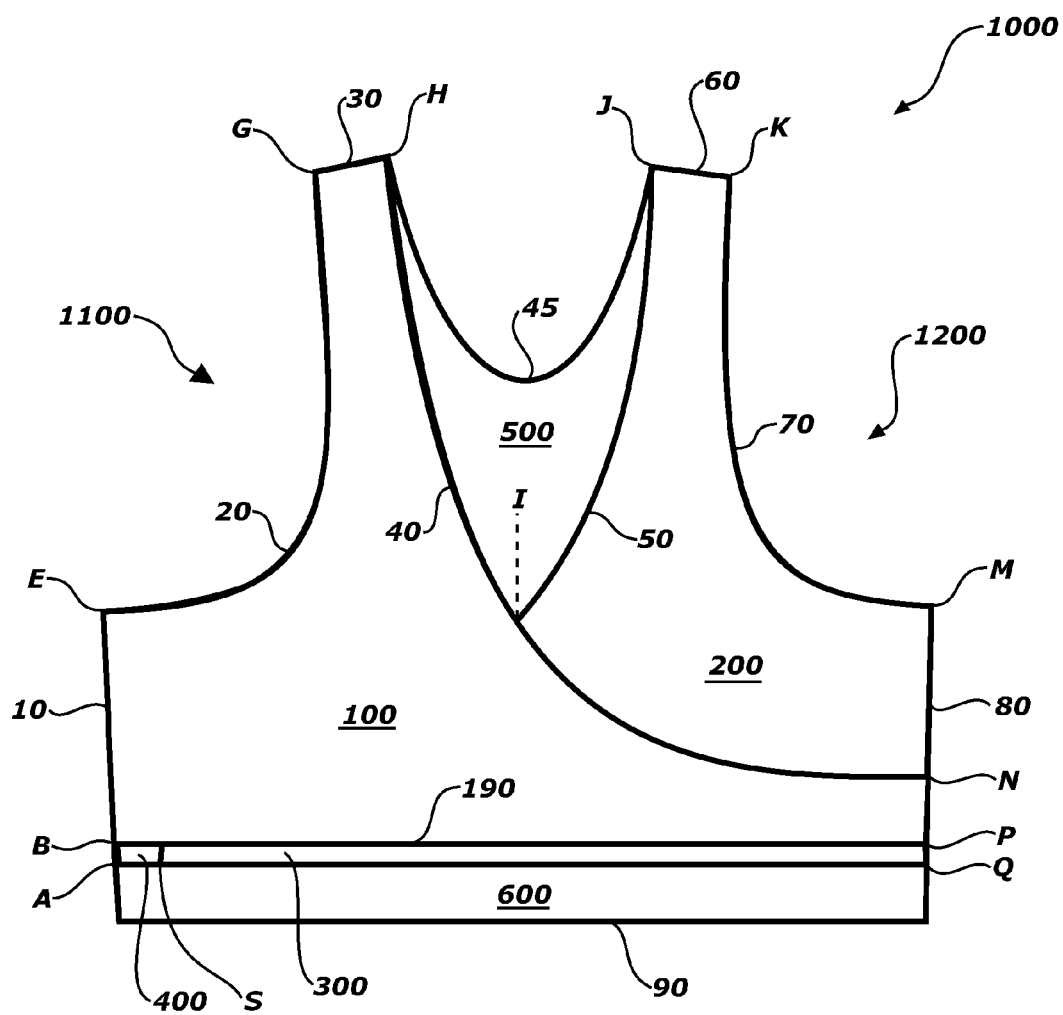

With reference to FIG. 8J, the fully constructed garment 1000 includes the right-chest component 1100, with its free edge, i.e., the right medial edge 40 that extends from point H at the right shoulder side 30 to point N at the left lateral side 80 of the garment 1000, and the left-chest component 1200, with its free edge, i.e., the left medial edge 50 that extends from point J at the left shoulder side 60 to point D at the right lateral side 10 of the garment 1000. The garment 1000 further includes the right outer layer 100 with its free edge, i.e., the lower edges 190 that extends from point B at the right lateral side 10 of the garment 1000 to point P at the left lateral side 80 of the garment 1000. The right inner layer 300 includes its free edge, i.e., the right lateral edge 310 (FIG. 8G) that extends from point S at the adjoined lower edges 390, 490 of the inner layers to point F at the adjoined upper right lateral edges 120, 320. The left outer layer 200 includes its free edge, i.e., the lower edge 290 (FIG. 8D) that extends from point C at the right lateral side 10 of the garment 1000 to point O at the left lateral side 80 of the garment 1000. The left inner layer 400 includes its free edge, i.e., the left lateral edge 480 (FIG. 8C) that extends from point L at the left upper lateral edge 70 to point R at the adjoined lower edges 390, 490 of the inner layers (i.e., the right inner layer 300 and the left inner layer 400).

Figure 9A:
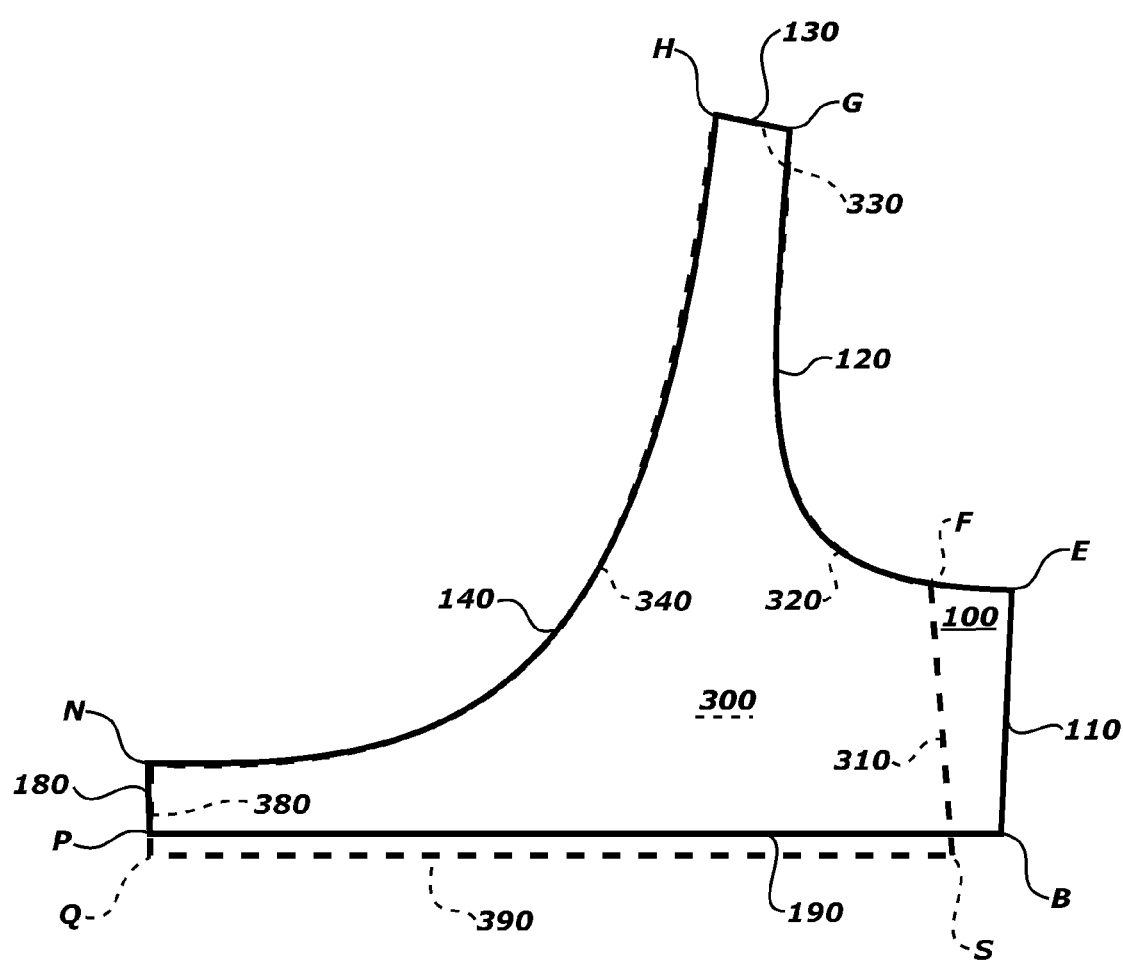
FIGS. 9A through 9F are rear, elevational illustrations of various components of the garment of FIG. 1, illustrated in order from front of the garment to back of the garment.
Figure 9B:
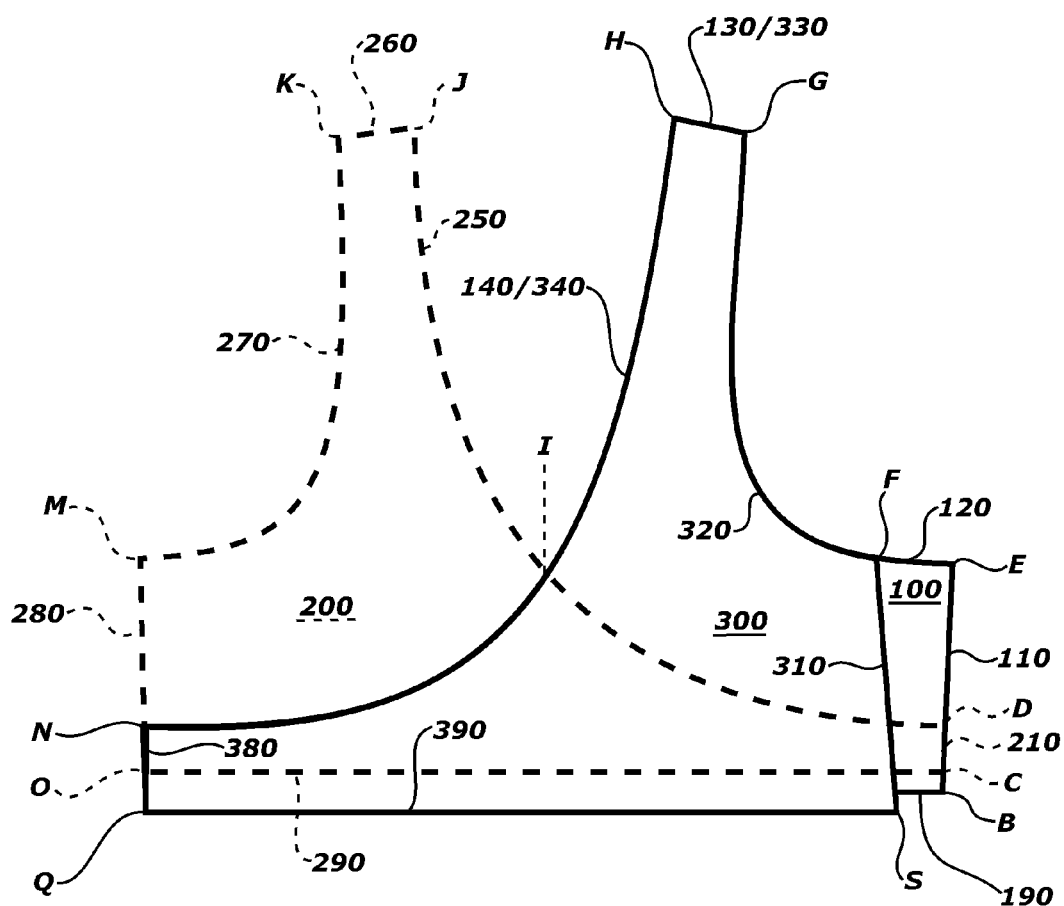
Figure 9C:
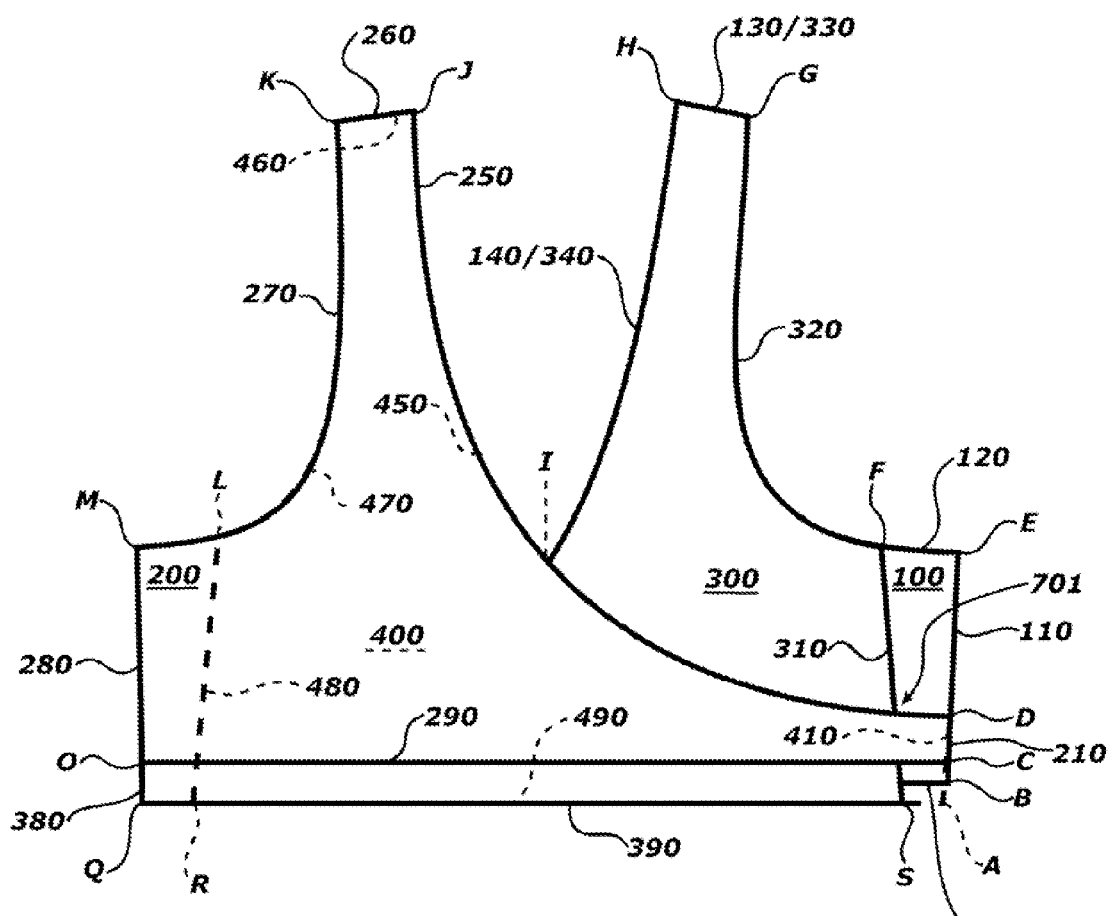

FIGS. 9A through 9F illustrate, in rear view, the various components of the garment 1000 in their respective dispositions, from front to back, in the same respective order as illustrated in the front view in FIGS. 8A through 8J. Thus, with reference to FIG. 9A, the right inner layer 300 is disposed behind (i.e., underlays) the right outer layer 100. With reference to FIG. 9B, the left outer layer 200 is disposed behind (i.e., underlays) the left inner layer 300. With reference to FIG. 9C, the left inner layer 400 is disposed behind (i.e., underlays) the left outer layer 200. In such arrangement, the right outer layer 100 and right inner layer 300 together cross in front of the left outer layer 200 and left inner layer 400.

Figure 9D:
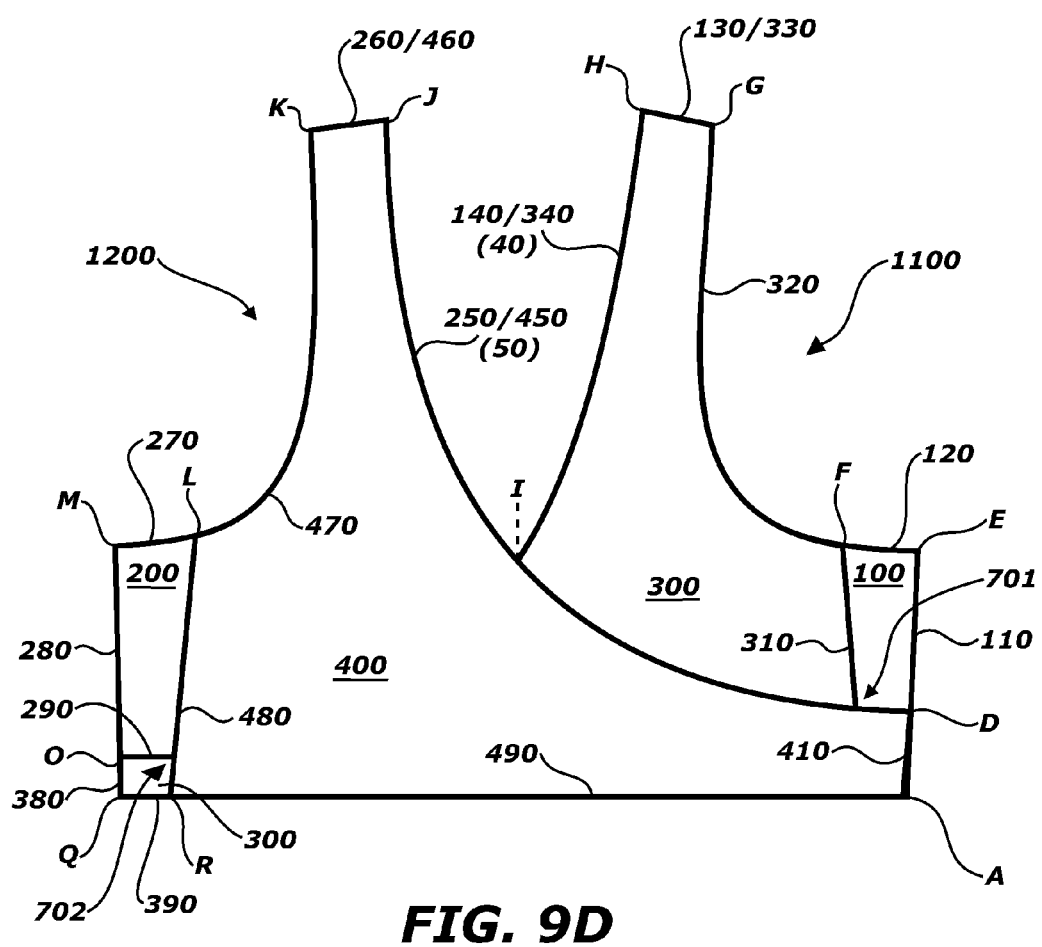

With reference to FIG. 9D, the right nook 701 is defined where the free edge of the right inner layer 300 crosses the free edge of the left-chest component 1200, i.e., where the right lateral edge 310 of the right inner layer 300 crosses over the left medial edge 50 of the left-chest component 1200 (i.e., the adjoined medial edges 250, 450 of the left outer layer 200 and left inner layer 400 of the left-chest component 1200). In the disengaged configuration illustrated in FIG. 9D, the right front layer 100 covers the right nook 701.

With further reference to FIG. 9D, the left nook 702 is defined where the free edge of the left inner layer 400 crosses the free edge of the left outer layer 200, i.e., where the left lateral edge 480 of the left inner layer 400 crosses over the lower edge 290 of the left outer layer 200. In the disengaged configuration illustrated in FIG. 9D, the extensions 102 (FIG. 3), 302 (FIG. 4) of the right-chest component 1100 cover the left nook 702.

Figure 9E:
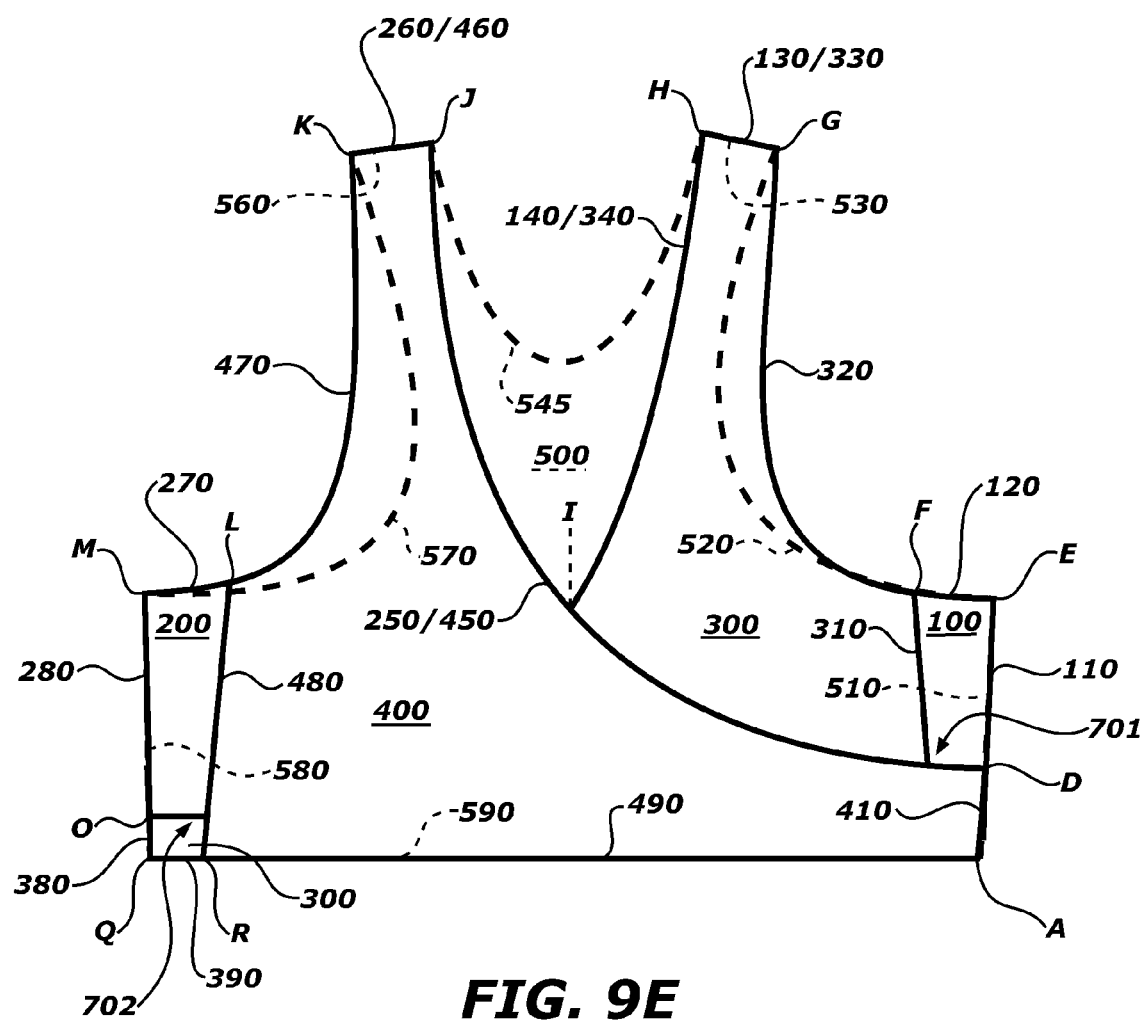
Figure 9F:
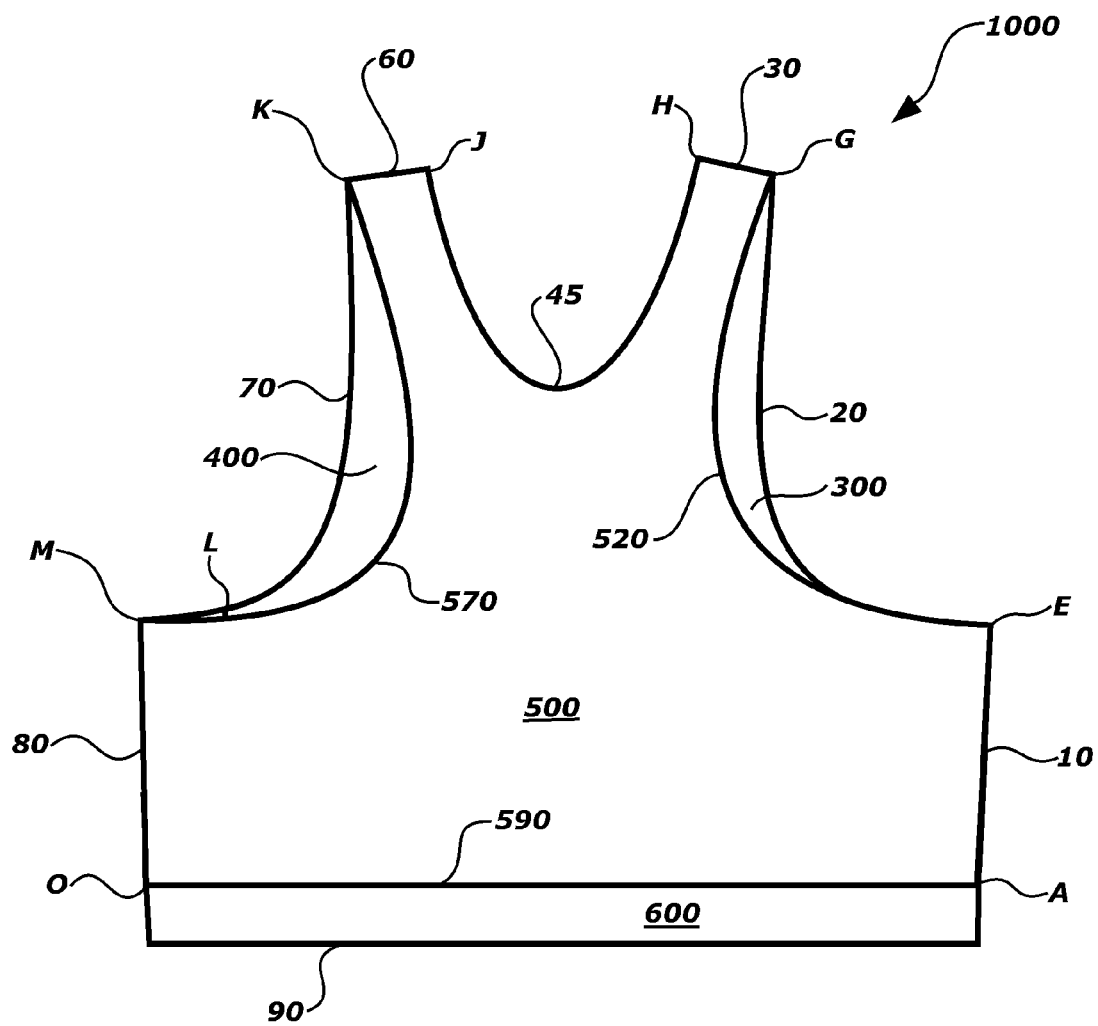

With reference to FIG. 9E, the back component 500 overlays the left inner layer 400, and, with reference to FIG. 9F, the rib band 600 is joined along the lower edge 90 of the garment 1000.

A method of constructing a garment (e.g., the garment 1000 (FIG. 1)) may include adjoining (e.g., stitching) the left outer layer 200 of a stretchable material to the left inner layer 400 of a stretchable material (which may be the same or a different stretchable material as the stretchable material of the left outer layer 200), to form the left-chest component 1200, and adjoining (e.g., stitching) the right outer layer 100 of a stretchable material to the right inner layer 300 of a stretchable material to form the right-chest component 1100. In forming the left-chest component 1200, the left outer layer 200 and the left inner layer 400 may be adjoined along, for example, medial edges 250, 450, along left shoulder edges 260, 40, and along corresponding lengths of upper left lateral edges 270, 470. In forming the right-chest component 1100, the right outer layer 100 and the right inner layer 300 may be adjoined along the left lateral edges 180, 380, along the medial edges 140, 340, along the right shoulder edges 130, 330, and along corresponding lengths of the upper right lateral edges 120, 320. The one of the chest components 1100, 1200 (e.g., the right-chest component 1100) may be positioned to overlap the another of the chest components 1100, 1200 (e.g., the left-chest component 1200). Then, the lower edges 190, 290 of the right outer layer 100 and the left outer layer 200, respectively, may be adjoined. Edges of the layers 100, 200, 300, 400 that occupy at least a portion of the distance between points Q and M may be adjoined to form the left lateral side 80 of the garment 1000, and edges of the layers 100, 200, 300, 400 that occupy at least a portion of the distance between points E and A may be adjoined to form the right lateral side 10 of the garment 1000. The back component 500 may be positioned as illustrated in FIG. 9E and adjoined to the front of the garment 1000 while the layer edges between points Q and M, between points K and J, between points H and G, and between points E and A are being adjoined. Alternatively, the front of the garment 1000 (i.e., the right-chest component 1100 and the left-chest component 1200) may be constructed with attached and free edges and then the back component 500 adjoined thereto. Finally, the rib band 600 may be adjoined to the lower edge 390 of the right inner layer 300, to the lower edge 490 of the left inner layer 400, and to the lower edge 590 of the back component 500.

In the resulting, constructed garment 1000, each of the layers 100, 200, 300, 400 includes one free edge, and each of the chest components 1100, 1200 includes at least one free edge (provided by adjoined, medial edges of the inner and outer layers of the respective chest component). For example, the right outer layer 100 includes the lower edge 190 as its one free edge; the right inner layer 300 includes the right lateral edge 310 as its one free edge; the right-chest component 1100 includes the right medial edge 40 as a free edge; the left outer layer 200 includes the lower edge 290 as its own free edge; the left inner layer 400 includes the left lateral edge 480 as its one free edge; and the left-chest component 1200 includes the left medial edge 50 as a free edge.

While the figures illustrate the back component 500 as a "racer back" piece, in other embodiments the back component 500 may include one or more sub-components, such as wings, adjustment straps, clasps, hooks, or other components enabling the securing of the garment 1000 to a wearer.

With reference to FIGS. 10 through 26, illustrated is the garment 1000 in various configurations, including a disengaged configuration (FIGS. 10 and 11), pumping configurations (FIGS. 18 and 23), and a nursing configuration (FIG. 26), along with transitions between configurations.

Figure 10:
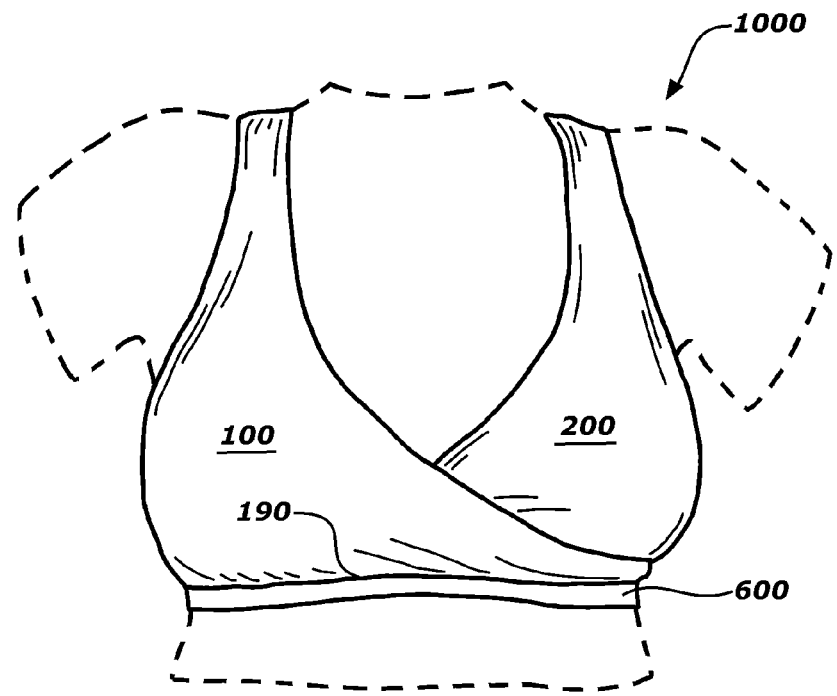
FIG. 10 is a front, elevational, perspective illustration of a garment, according to an embodiment of the present disclosure, in a disengaged configuration.
Figure 11:
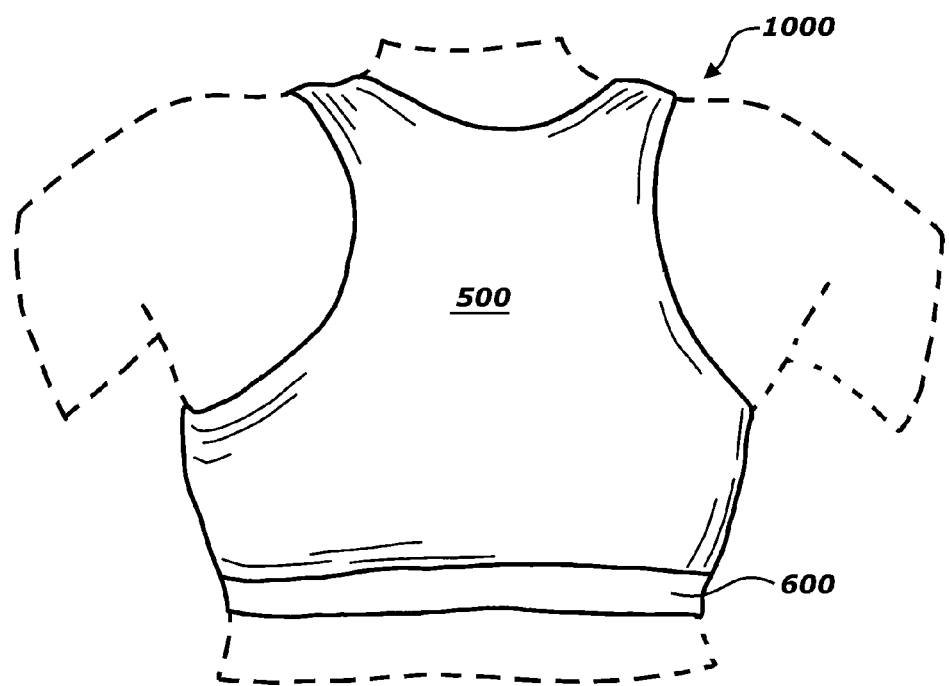
FIG. 11 is a rear, elevational, perspective illustration of the garment of FIG. 10.

With reference to FIGS. 10 and 11, illustrated is the garment 1000 in a disengaged configuration. In such configuration, the right outer layer 100 and the left outer layer 200 fully conceal the breasts, and the garment 1000 may visually appear to be a conventional brassiere with seamless, continuous cups, i.e., lacking any defined wholes or slits in the cups proximate to the nipples of the breasts.

Figure 12:
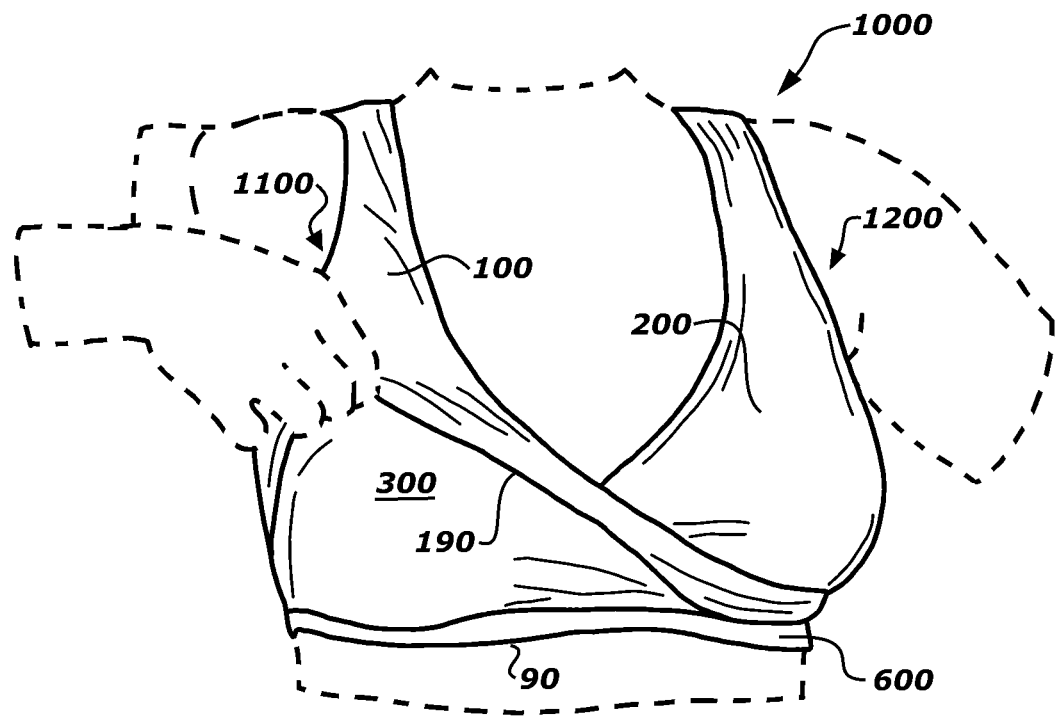
FIG. 12 is a front, elevational, perspective illustration of the garment of FIG. 10, in a configuration in transition between the disengaged configuration of FIG. 10 and a right-pumping configuration (see FIG. 18).
Figure 13:
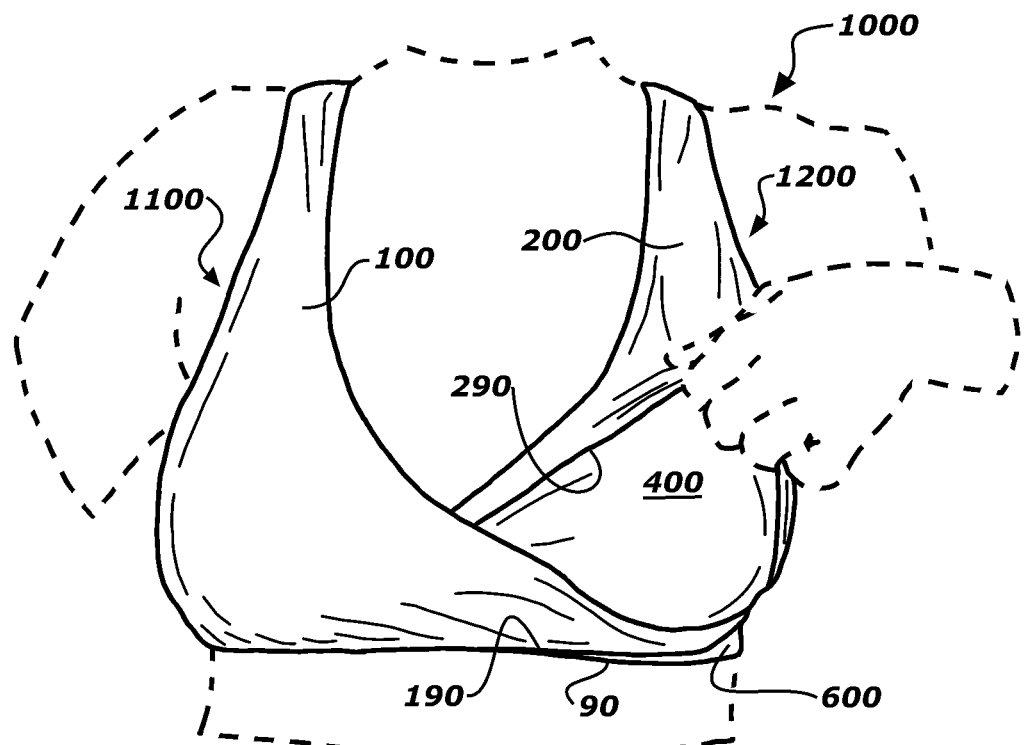
FIG. 13 is a front, elevational, perspective illustration of the garment of FIG. 10, in a configuration in transition between the disengaged configuration of FIG. 10 and a left-pumping configuration (see FIG. 23).

With reference to FIGS. 12 and 13, illustrated are stages in which the garment 1000 is being transitioned between the disengaged configuration of FIG. 10 to a pumping configuration (see FIGS. 18 and 23), in which the garment 1000 is enabled to receive the funnel 5 (FIG. 15) of a breast pump, such that the wearer may express milk using the breast pump.

To begin the transition, the free edge (e.g., the lower edge) of an outer layer of at least one of the chest components 1100, 1200 is pulled away from its disengaged position. For example, to transition toward a right-pumping configuration (FIG. 18), the lower edges 190 of the right outer layer 100 of the right-chest component 1100 is pulled away from its disengaged position, i.e., it is pulled away from the lower edge 90 of the garment 1000, exposing the right inner layer 300. At such a stage in the transition, the nipple of the right breast and a majority of the right breast are still concealed.

Alternatively or additionally, as illustrated in FIG. 13, to transition from the disengaged configuration of FIG. 10 to a left-pumping configuration (FIG. 23), the lower edge 290 of the left outer layer 200 of the left-chest component 1200 is pulled away from its disengaged position, i.e., it is pulled away from the lower edge 90 of the garment 1000, exposing the left inner layer 400. At such a stage in the transition, the nipple of the left breast and a majority of the left breast are still concealed.

Figure 14:
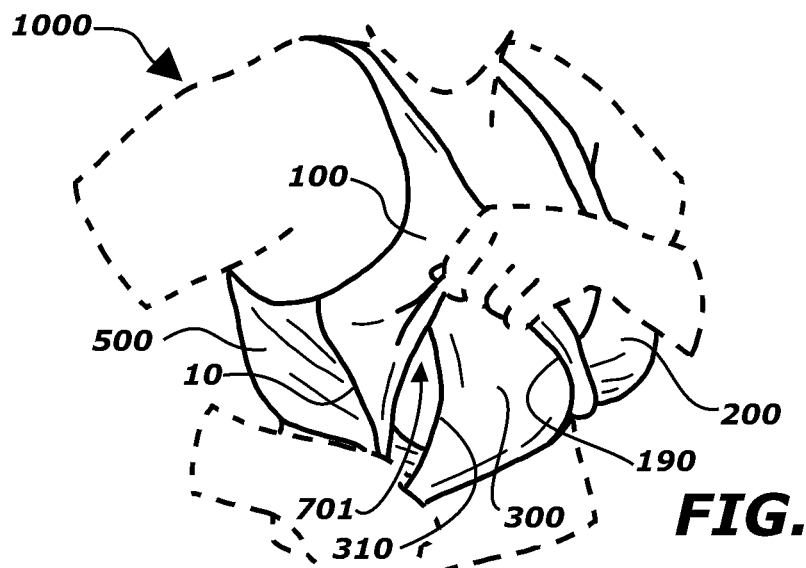
FIGS. 14 through 17 are front and right-side, elevational, perspective illustrations of the garment of FIG. 10, in whole or in part, in configurations transitioning, respectively, between the configuration of FIG. 12 and the right-pumping configuration (see FIG. 18).

With reference to FIGS. 14 and 15, further transitioning toward the right-pumping configuration (FIG. 18), after the stage illustrated in FIG. 12, the funnel 5 of the breast pump may be inserted into the right nook 701 and behind the free edge of the right inner layer 300, i.e., behind the right lateral edge 310. The right lateral edge 310 is pulled away from its disengaged position, i.e., pulled away from the right lateral side 10 of the garment 1000, to enable the funnel 5 to be moved over the right nipple.

Figure 16:
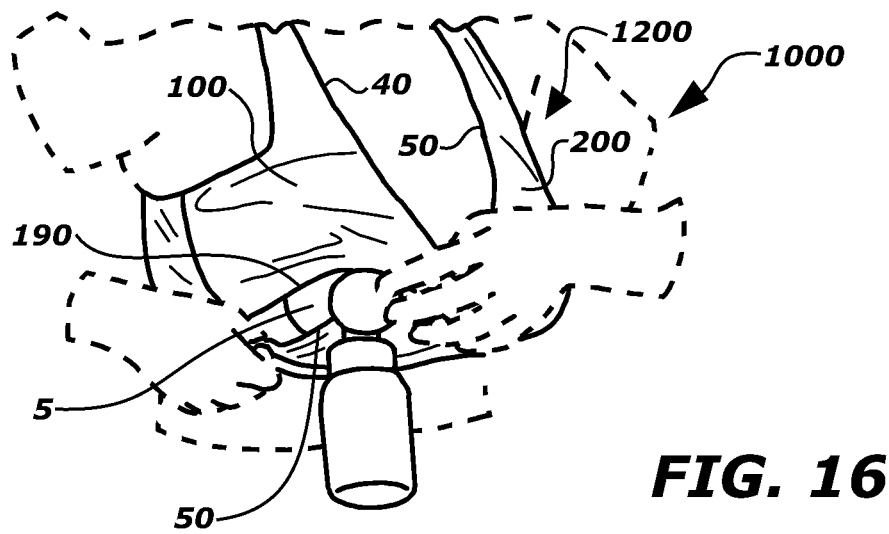
Figure 17:
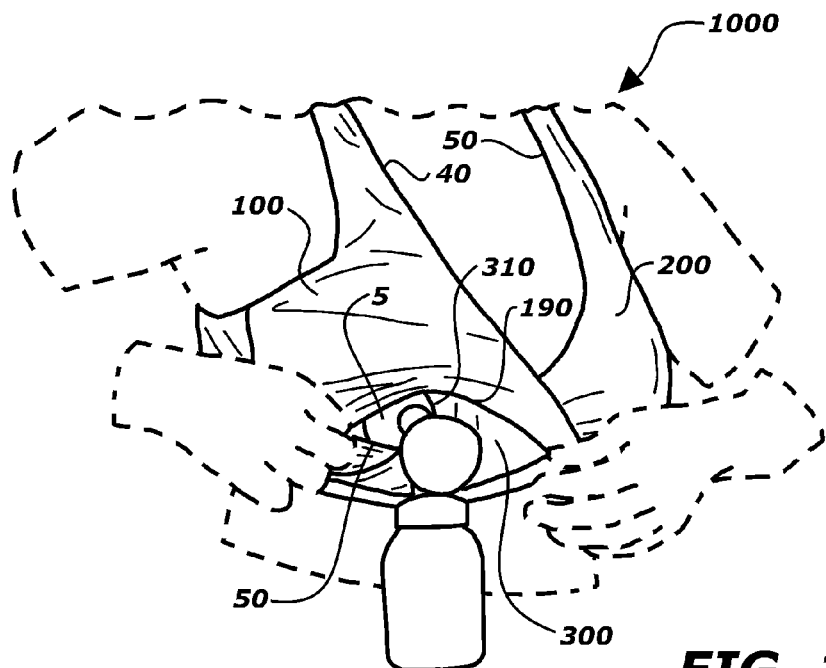

With reference to FIG. 16, the free edge (i.e., the left medial edge 50) of the left-chest component 1200 is pulled up and over the funnel 5 to its highest position. With reference to FIG. 17, the free edge (i.e., the lower edge 190) of the right outer layer 100 is lowered to cover an upper area of the funnel 5. Thus, as illustrated in FIG. 18, the garment 1000 is transitioned to the right-pumping configuration.

In the right-pumping configuration, three edges of the garment 1000 (i.e., the free edges of right outer layer 100, the right inner layer 300, and the left-chest component 1200, i.e., the lower edge 190 of the right outer layer 100, the right lateral edge 310 of the right inner layer 300, and the left medial edge 50 of the left-chest component 1200) secure the funnel 5 over the nipple. Each of the free edges inhibit the funnel 5 from moving out of place. For example, the left medial edge 50 of the left-chest component 1200 supports the funnel 5 substantially from below the funnel 5 and inhibits the funnel 5 from slipping down the breast. The right lateral edge 310 of the right inner layer 300 supports the funnel 5 substantially from the left side of the funnel 5 and inhibits the funnel 5 from moving medially. The lower edge 190 of the right outer layer 100 supports the funnel 5 substantially from above and to the right side of the funnel 5 and inhibits the funnel 5 from falling away from the nipple or shifting laterally.

The funnel 5 may be disengaged from the garment 1000, while the garment 1000 is still worn by the woman, by moving the free edges away from the funnel 5 and removing the funnel 5 from the right nook 701 (FIG. 14).

Figure 19:
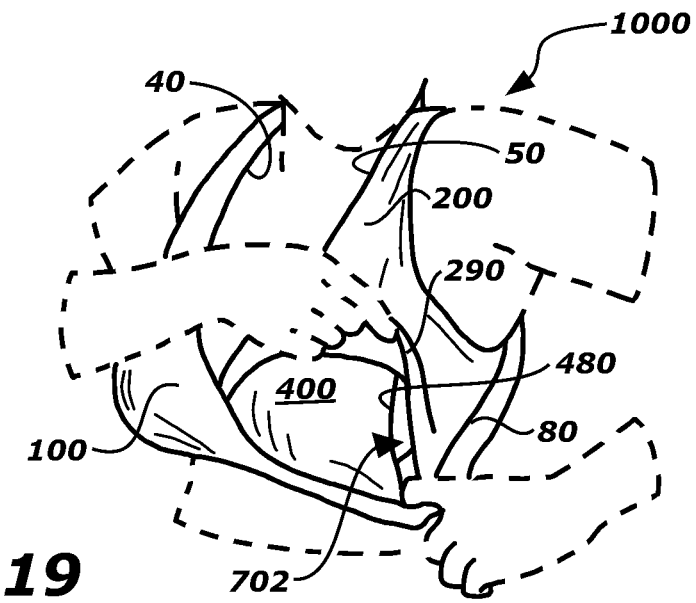
FIGS. 19 through 22 are front and left-side, elevational, perspective illustrations of the garment of FIG. 10, in whole or in part, in configurations transitioning, respectively, between the configuration of FIG. 13 and the left-pumping configuration (see FIG. 23).
Figure 20:
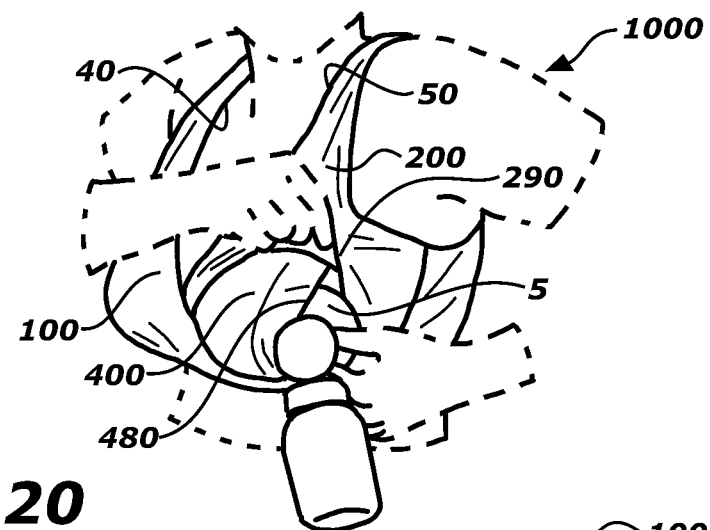

With reference to FIGS. 19 and 20, in transitioning toward the left-pumping configuration (FIG. 23) from the disengaged configuration (FIG. 10), after the stage illustrated in FIG. 13, the funnel 5 of the breast pump may be inserted into the left nook 702 and behind the free edge of the left inner layer 400, i.e., behind the left lateral edge 480. The left lateral edge 480 is pulled away from its disengaged position, i.e., pulled away from the left lateral side 80 of the garment 1000, to enable the funnel 5 to be moved over the left nipple.

Figure 21:
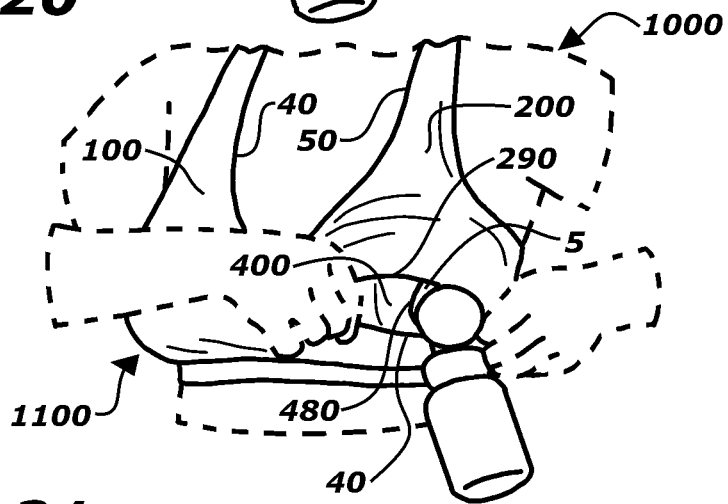
Figure 22:
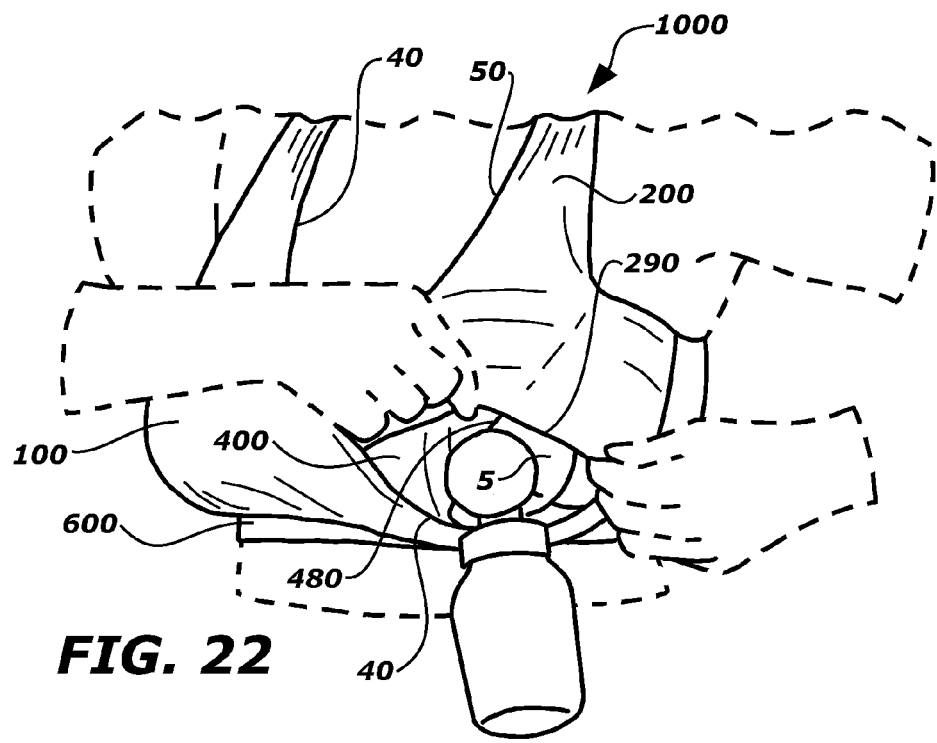

With reference to FIG. 21, the free edge (i.e., the right medial edge 40) of the right-chest component 1100 is pulled up and over the funnel 5 to its highest position. With reference to FIG. 22, the free edge (i.e., the lower edge 290) of the left outer layer 200 is lowered to cover an upper area of the funnel 5. Thus, as illustrated in FIG. 23, the garment 1000 is transitioned to the left-pumping configuration.

In the left-pumping configuration, three edges of the garment 1000 (I.e., the free edges of the left outer layer 200, the left inner layer 400, and the right-chest component 1100, i.e., the lower edge 290 of the left outer layer 200, the left lateral edge 480 of the left inner layer 400, and the right medial edge 40 of the right-chest component 1100) secure the funnel 5 over the nipple. Each of the free edges inhibit the funnel 5 from moving out of place. For example, the right medial edge 40 of the right-chest component 1100 supports the funnel 5 substantially from below the funnel 5 and inhibits the funnel 5 from slipping down the breast. The left lateral edge 480 of the left inner layer 400 supports the funnel 5 substantially from the right side of the funnel 5 and inhibits the funnel 5 from moving medially. The lower edge 290 of the left outer layer 200 supports the funnel 5 substantially from above and to the left side of the funnel 5 and inhibits the funnel 5 from falling away from the nipple or shifting laterally.

Accordingly, the garment 1000 is configured to provide multi-directional (e.g., tri-directional) support to the funnel 5 to enable hands-free pumping. Moreover, the funnel 5 may be inserted in the garment 1000, removed from the garment 1000, or both without doffing (i.e., without the wearer removing) the garment, without attaching or detaching pieces of the garment 1000, such as flaps, patches, latches, hooks, uncomfortable straps, and without exposing the nipple or a majority of the breast.

Though FIGS. 18 and 23 illustrate hands-free pumping with only one funnel 5 received in the garment 1000, a pair of funnels 5 may be received in the pair of nooks (i.e., in the right nook 701 and the left nook 702) to enable hands-free pumping from both breasts simultaneously.

The material of the components and layers of the garment 1000 may be a stretchable material. As such, the stretch of the free edges of the respective layers and components, for receipt of the funnel 5, results in an elastic-like pull against the funnel 5, itself, when it is in place over the nipple, from the free edges supporting the funnel 5 (e.g., two free edges of each of the outer layer and inner layer of one chest component and a free edge of another chest component, such free edge formed by adjoined edges of the outer and inner layers of the another chest component). Moreover, according to embodiments of the present disclosure, the free edges of the outer layers 100, 200 (i.e., lower edges 190, 290) encourage the funnel 5 to remain on the upper part of the breast above the nipple; the free edges of the inner layers 300, 400 (i.e., lateral edges 310, 480) encourage the funnel 5 to stay centered on the breast and enable placement of the funnel 5 correctly over the unique nipple location of the wearer; and the free edges of the other chest component (i.e., the right medial edge 40 of the right-chest component 1100 for the left-pumping configuration and the left medial edge 50 of the left-chest component 1200 for the right-pumping configuration) inhibit the funnel 5 from slipping off the breast or at the bottom of the breast under the nipple. The elasticity of the stretchable material of each of the layers and components at all three points of support against the funnel 5, further discourages the funnel 5 from slipping outwardly away from the nipple or breast. The stretchable material of the garment 100 is further configured, in this way, to accommodate the natural expansion and contraction of a nursing woman's breasts as well as the natural variations in nipple locations on various women's breasts. The garment's 1000 funnel-receiving nooks (e.g., the right nook 701, the left nook 702), which may be substantially triangular and provide the multi-angled (e.g., tri-angled) funnel support in the pumping configurations, are therefore flexible and are not openings with fixed dimensions or disposition relative to the cup of the garment 1000.

Figure 26:
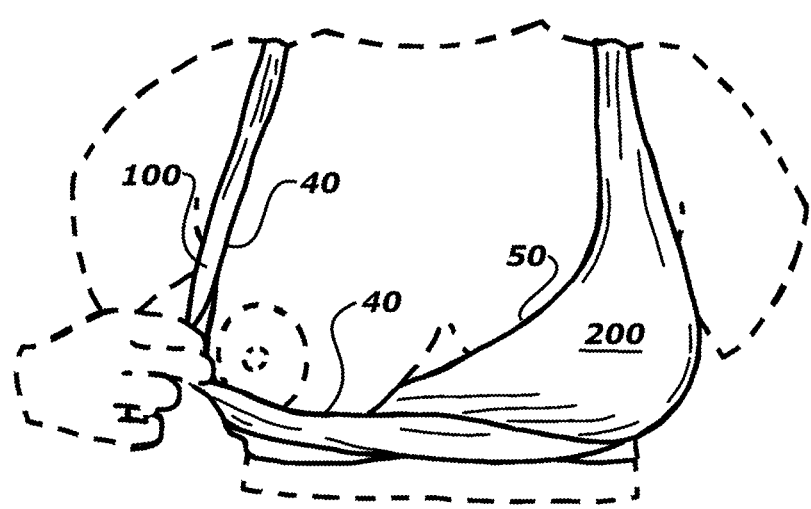
FIG. 26 is a front, elevational, perspective illustration of the garment of FIG. 10 in a right-nursing configuration.

With reference to FIG. 26, in some embodiments, the garment 100 may also be configured to be used to directly nurse an infant. To do so, a medial edge (e.g., the right medial edge 40, as illustrated, or the left medial edge 50) may be pulled down from its position in the disengaged configuration. Such pulling eventually exposes the breast and enables access to the breast by the infant. Therefore, a wearer may directly nurse an infant without manipulation of any clasps or buckles, without having to remove the garment 1000, and without having to detach any part of the garment 1000 from the rest of the garment 1000.

The garment 1000 may enable the wearer to directly nurse one infant from one breast while one chest component is in use in the nursing configuration (e.g., while the right-chest component 1100 is manipulated to expose the right breast in the right nursing configuration of FIG. 26), either while the other breast is concealed (e.g., while the left-chest component 1200 is in its disengaged configuration position, as in FIG. 26) or while the other breast is simultaneously engaged with the funnel 5 in a pumping configuration (e.g., while the left-chest component 1200 is in the left-pumping configuration position, as in FIG. 23). The garment 1000 may also allow the direct nursing of two infants, each from one breast, with both chest components 1100, 1200 in position of a nursing configuration (i.e., with not only the right-chest component 1100 manipulated to expose the right breast, as in FIG. 26, but also with the left-chest component 1200 manipulated to simultaneously expose the left breast). The garment 100 may also allow pumping from each breast simultaneously, with the right-chest component 1100 in its right-pumping configuration position, as in FIG. 18, and with the left-chest component 1200 in its left-pumping configuration position, as in FIG. 18. Thus, the garment 1000 provides flexibility in use to enable independent positioning of each of the chest components 1100, 1200 in any of the disengaged, pumping, and nursing configurations.

Moreover, at least in embodiments in which the right outer layer 100, the right inner layer 300, the left outer layer 200, and the left inner layer 400 are seamless, continuous material layers, the garment 100 is configured to cover and fully conceal the nipple and the breast when the layers are not being stretched to receive the funnel 5 of a breast pump, i.e., when in the disengaged configuration. As such, the garment 1000 may have a visible appearance akin to the appearance of a conventional crossover brassiere. Further, the seamless, continuous inner layers 300, 400 are configured to cover the nipple and the breast when the inner layers 300, 400 are not being stretched. Accordingly, when the outer layers 100, 200 of the garment 1000 are stretched to insert the funnel 5 of a breast pump, the breast may not be exposed, but may remain substantially concealed by the outer layers 100, 200 and inner layer 300, 400.

Accordingly, the garment 100 may be worn in the same manner as a conventional brassiere, e.g., for long periods of time, as an undergarment, or may be configured as outerwear. The garment 1000 may allow for quick and easy, hands-free use of a breast pump with the funnel 5 or a pair of breast pumps each with the funnel 5 without having to disrobe or otherwise remove the garment 1000 or any part of the garment 1000. The central area of each cup of the garment 1000 (i.e., the areas of the layers and components interior to the peripheral edges and sides) may comprise only material, thereby adding to the relative comfort of the garment 1000.

Figure 24:
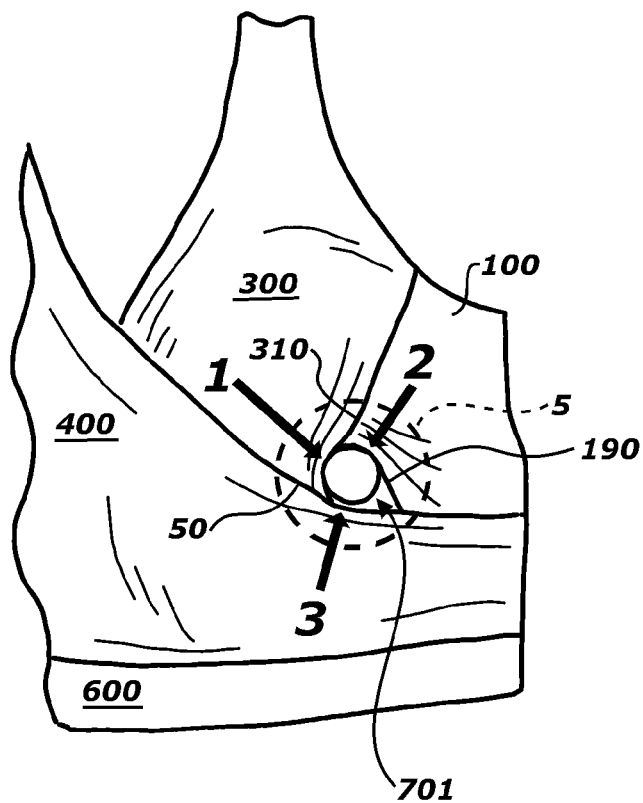
FIG. 24 is a rear, elevational, perspective, partial illustration of the garment of FIG. 10, in the right-pumping configuration of FIG. 18.
Figure 25:
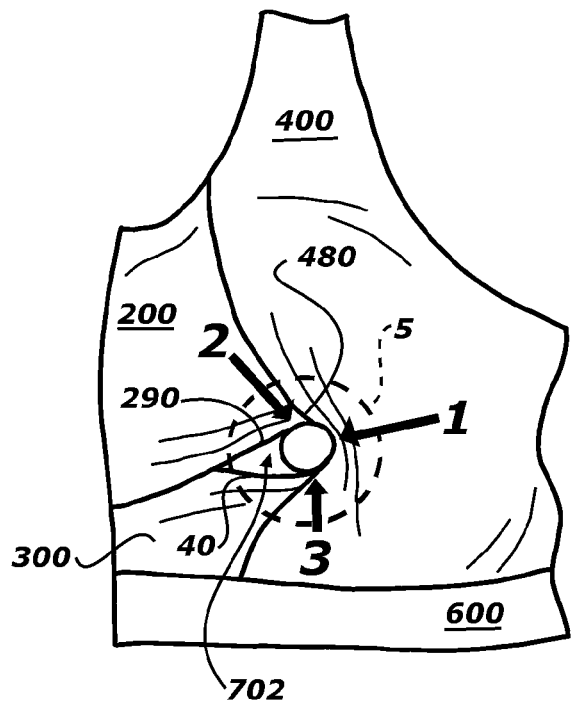
FIG. 25 is a rear, elevational, perspective, partial illustration of the garment of FIG. 10, in the left-pumping configuration of FIG. 23.

Further, the configuration of the garment 1000 may enable a wearer to support the funnel 5 against her nipple, hands free, regardless of whether the nipple is located in the exact center of the breast or is offset somewhat. For example, with reference to FIGS. 24 and 25, illustrated are interior views of the right-pumping configuration of FIG. 18 and the left-pumping configuration of FIG. 25. As illustrated, the funnels 5 are supported in at least three directions, indicated by arrows 1 through 3. The elasticity of the material of the layers and components of the garment 1000 enable the funnel 5 to be selectively shifted by the wearer proximate to a center of the cup. Regardless of where, in this region, the funnel 5 is shifted by the wearer, the funnel will retain support from the multiple directions (arrows 1 through 3). Nonetheless, the triangular nooks (e.g., the right nook 701, the left nook 702) defined by the overlapping free edges provide an adjustable opening, rather than a static, fixed-dimension, fixed location "hole" or slit that limits the relative positioning of the funnel 5 to the breast of the wearer. Still further, because the funnel 5 is supported by each of the multiple layers or components in multiple directions or angles using the garment 1000 itself, the wearer may not need to hassle with separate attachment mechanisms or attachment devices such as hooks, buttons, zippers, hook and loop connections, or the like. Also, because the multiple layers or components of the garment 100 support the funnel 5 from multiple (e.g., three) directions, this may decrease the likelihood that the funnel 5 will move away from the nipple undesirably during hands-free pumping.

Specific embodiments have been shown by way of example in the drawings and have been described in detail here. However, the disclosed garments are susceptible to various modifications and alternative forms in implementation. For example, garments according to the present disclosure may be configured as a tank brassiere, a halter top, a sports brassiere, or other undergarment. The garments may alternatively or additionally be incorporated within outerwear, such as in a tank top, a bathing suit, a leotard, a shirt, or other outergarment. The wearer may also wear the garment, according to embodiments of the present disclosure, with a nursing pad or other soft pad inserted between the outer layers 100, 200 and their respective inner layers 300, 400. Additionally or alternatively, the free edges and adjoined edges of the garment 1000 may be disposed at different locations in the garment 1000 and still overlap in such a manner as to provide nooks adjustable to receive funnels. Moreover, the left-chest component 1200 may overlap the right-chest component 1100. In some embodiments, the back component 500 may be configured to include a conventional brassiere closure (e.g., with claps), configured as a pullover standard back component, or another conventional back component of a conventional women's support garment. Some embodiments of the present disclosure may be configured to enable transitioning between the disengaged configuration and the pumping configurations, but without enabling a direct-nursing configuration. Nonetheless, it should be understood that the present disclosure is not intended to be limited to the particular forms disclosed. Rather, the present invention encompasses all modifications, combinations, equivalents, variations, and alternatives falling within the scope of the present disclosure as defined by the following appended claims and their legal equivalents.

What is claimed is:

1. A garment for a nursing woman, the garment comprising:

material layers of a chest component of a front side of the garment, the material layers extending between a left lateral side of the garment, a right lateral side of the garment, and a shoulder strap of the garment, the material layers of the chest component at least partially overlapping one another to define, by an edge of one of the material layers and an edge of another of the material layers, a nook proximate one of the left lateral side of the garment and the right lateral side of the garment.

2. The garment of claim 1, wherein the material layers of the chest component comprise a stretchable material.

3. The garment of claim 1, wherein the material layers of the chest component are seamless and continuous material layers.

4. The garment of claim 1, wherein the nook is substantially triangular shaped and is defined by a lower edge of one of the material layers of the chest component, a lateral edge of another of the material layers of the chest component, and a medial edge of another chest component.

5. The garment of claim 1:
further comprising another shoulder strapl;
wherein the chest component comprises a pair of the material layers; and
further comprising another chest component of the front side of the garment, the another chest component comprising another pair of material layers extending between the left lateral side of the garment, the right lateral side of the garment, and the another shoulder strap, the material layers of the another chest component at least partially overlapping one another to define, by an edge of one of the material layers of the another pair of material layers and an edge of another of the material layers of the another pair of material layers, another nook proximate to another one of the left lateral side of the garment and the right lateral side of the garment.

6. The garment of claim 5, wherein:
the pair of the material layers comprises an outer layer and an inner layer; and
the another pair of the material layers comprises another outer layer and another inner layer.

7. The garment of claim 5, wherein:
the material layers of the pair of the material layers are affixed to one another along a medial edge of each of the material layers of the pair to define a medial edge of the chest component; and
the material layers of the another pair of the material layers are affixed to one another along a medial edge of each of the material layers of the another pair to define a medial edge of the another chest component.

8. The garment of claim 7, wherein:
the edge of the one of the material layers is a free edge of the one of the material layers;
the edge of the another of the material layers is a free edge of the another of the material layers; and
the garment is configured to transition between a disengaged configuration and a pumping configuration, wherein the nook is defined by
the free edge of the one of the material layers of the chest component,
the free edge of the another of the material layers of the chest component, and
the medial edge of the another chest component.

9. The garment of claim 7, wherein:
the edge of one of the material layers of the another pair of material layers is a free edge of the one of the material layers of the another pair of material layers;
the edge of the another of the material layers of the another pair of material layers is a free edge of the another of the material layers of the another pair of material layers; and
the garment is configured to transition between a disengaged configuration and a pumping configuration, wherein the another nook is defined by
the free edge of the one of the material layers of the another pair of the material layers,
the free edge of the another of the material layers of the another pair of material layers, and
the medial edge of the chest component.

10. The garment of claim 7, wherein the medial edge of the chest component and the medial edge of the another chest component are not directly attached to one another.

11. The garment of claim 7, wherein the medial edge of the chest component and the medial edge of the another chest component cross one another proximate to a medial centerline of the garment.

12. A garment for a nursing woman, the garment comprising:
a back component extending along a rear side of the garment between a left lateral side of the garment and a right lateral side of the garment;
a left-chest component extending along a front side of the garment between the left and right lateral sides of the garment, the left-chest component comprising:
a left outer material layer extending between the left and right lateral sides of the garment, the left outer material layer joined to the back component along at least a portion of each of the left and right lateral sides of the garment; and
a left inner material layer extending from the right lateral side of the garment toward the left lateral side of the garment, the left inner material layer defining a left free edge medially disposed to the left lateral side of the garment, the left inner material layer joined to the left outer material layer and to the back component along at least a portion of the right lateral side of the garment; and
a right-chest component extending along the front side of the garment between the left and right lateral sides of the garment, the right-chest component comprising:
a right outer material layer extending between the left and right lateral sides of the garment, the right outer material layer joined to the back component along at least a portion of each of the left and right lateral sides of the garment; and
a right inner material layer extending from the left side of the garment toward the right lateral side of the garment, the right inner material layer defining a right free edge medially disposed to the right lateral side of the garment, the right inner material layer joined to the right outer material layer and to the back component along at least a portion of the left lateral side of the garment.

13. The garment of claim 12, wherein:
the left outer material layer defines a free lower edge of the left outer material layer; and
the right outer material layer defines a free lower edge of the right outer material layer.

14. The garment of claim 12, wherein:
the left free edge of the left inner material layer extends substantially vertically from a lower edge of the garment; and
the right free edge of the right inner material layer extends substantially vertically from the lower edge of the garment.

15. The garment of claim 12, wherein the left inner material layer is joined, along a lower edge of the right inner material layer, to the right inner material layer, along a lower edge of the right inner material layer.

16. A garment for a nursing woman, the garment comprising:
a left-chest component for a front side of the garment, comprising:

a left outer material layer; and a left inner material layer, the left outer material layer and the left inner material layer attached to one another along at least one attached edge of the left-chest component, and the left outer material layer at least partially overlaying a free edge of the left inner material layer; and a right-chest component for a front side of the garment, comprising:

a right outer material layer; and a right inner material layer, the right outer material layer and the right inner material layer attached to one another along at least one attached edge of the right-chest component, and the right outer material layer at least partially overlaying a free edge of the right inner material layer, a medial edge of the left-chest component crossing a medial edge of the right-chest component.

17. The garment of claim 16, wherein the left outer material layer includes a free lower edge, all other edges of the left outer material layer being attached edges.

18. The garment of claim 16, wherein the right outer material layer includes a free lower edge, all other edges of the right outer material layer being attached edges.

19. The garment of claim 16, wherein a periphery of the right inner material layer is defined by the free edge of the right inner material layer and attached edges of the right inner material layer.

20. The garment of claim 16, wherein a periphery of the left inner material layer is defined by the free edge of the left inner material layer and attached edges of the left inner material layer.

\* \* \* \* \*